(12) United States Patent
Yao et al.

(10) Patent No.: US 9,868,734 B2
(45) Date of Patent: Jan. 16, 2018

(54) CONJUGATE OF BENZOFURANONE AND INDOLE OR AZAINDOLE, AND PREPARATION AND USES THEREOF

(71) Applicant: Luoda Biosciences, Inc., Chuzhou, Anhui (CN)

(72) Inventors: Qizheng Yao, Anhui (CN); Jiajia Liu, Anhui (CN); Zhaohui Wang, Anhui (CN); Kui Wu, Anhui (CN); Yongbin Wang, Anhui (CN); Shining Yao, Anhui (CN); Ruihuan Chen, Anhui (CN); Beibei Yang, Anhui (CN)

(73) Assignee: Luoda Biosciences, Inc., Anhui (CN)

( * ) Notice: Subject to any disclaimer, the term of this patent is extended or adjusted under 35 U.S.C. 154(b) by 0 days.

(21) Appl. No.: 14/779,719

(22) PCT Filed: May 26, 2014

(86) PCT No.: PCT/CN2014/000525
§ 371 (c)(1),
(2) Date: Mar. 14, 2016

(87) PCT Pub. No.: WO2014/190758
PCT Pub. Date: Dec. 4, 2014

(65) Prior Publication Data
US 2016/0185771 A1    Jun. 30, 2016

(30) Foreign Application Priority Data

May 28, 2013    (CN) .......................... 2013 1 0202029

(51) Int. Cl.
*C07D 471/04*    (2006.01)
*C07D 405/04*    (2006.01)
*C07D 491/00*    (2006.01)

(52) U.S. Cl.
CPC ......... *C07D 471/04* (2013.01); *C07D 405/04* (2013.01); *C07D 491/00* (2013.01)

(58) Field of Classification Search
None
See application file for complete search history.

(56) References Cited

U.S. PATENT DOCUMENTS 8,642,765 B2    2/2014    Cheng et al.

FOREIGN PATENT DOCUMENTS

| CN | 101023944 | 8/2007 |
|---|---|---|
| CN | 101074229 | 11/2007 |
| CN | 101492448 | 7/2009 |
| CN | 101492465 | 7/2009 |
| CN | 101704813 | 5/2010 |
| CN | 101747339 | 6/2010 |
| CN | 103333161 | 10/2013 |
| EP | 2199292 | 6/2010 |
| WO | 0024736 A1 | 5/2000 |
| WO | 2010072399 | 7/2010 |

OTHER PUBLICATIONS

CAPLUS 1955:27916.*
International Search Report in International Application No. PCT/CN2014/000525 dated Sep. 9, 2014.
Libnow, et al., "First synthesis of oxa-analogous isoindigo-N-glycosides", Tetrahedron Letters, vol. 49, pp. 289-291, (2008).

* cited by examiner

*Primary Examiner* — Heidi Reese
(74) *Attorney, Agent, or Firm* — Greenberg Traurig, LLP; Fang Xie

(57) ABSTRACT

The present invention relates to an oxo indirubin or isoindigo derivative, an oxo aza indirubin or isoindigo derivative, and their optical isomers, racemes, cis/trans isomers and pharmaceutically acceptable salts, which can be used for preparing a drug for treating or preventing diseases such as glucose metabolic disorder, inflammatory or autoimmune disease, neurodegenerative disease, a mental illness, tissue proliferation disease or tumors.

13 Claims, 2 Drawing Sheets

(a)

(b)

(d1)

(d2)

(d3)

Figure 1:
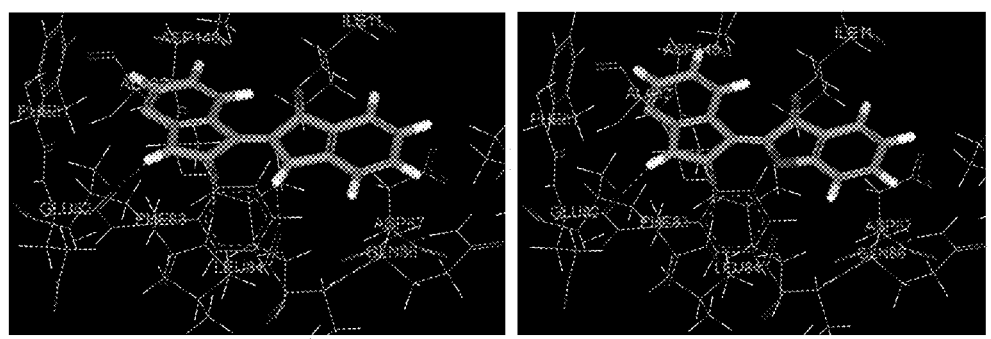
Figure 1:
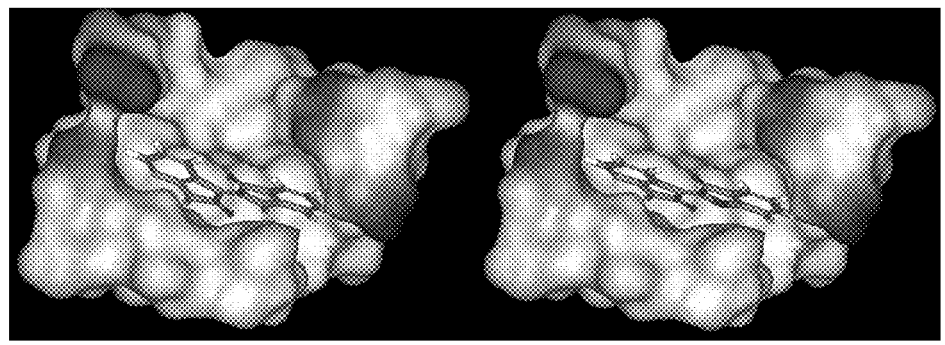

CONJUGATE OF BENZOFURANONE AND INDOLE OR AZAINDOLE, AND PREPARATION AND USES THEREOF

CROSS REFERENCE TO RELATED APPLICATIONS

This application is a national phase filing under 35 U.S.C. 371 of International Application No. PCT/CN2014/000525, filed May 26, 2014, which claims priority to Chinese Patent Application No. CN201310202029.3, filed May 28, 2013, the disclosures of each of which are incorporated herein by reference in their entireties.

TECHNICAL FIELD

The present invention relates to designs, preparation methods, pharmaceutical compositions and uses of a class of novel chemical entities containing the novel scaffolds of 1'-oxo-(aza)indirubin or 1'-oxo-(aza)isoindigo. This type of molecules couples (aza)indole with benzofuranone to form an extended pi-conjugated system, which is chemically distinct from but structurally similar to bi-(aza)indoles.

BACKGROUND

Indirubin (3, 2'-bi-indole) and its isoform, isoindigo (3, 3'-bi-indole) are the active antitumor components isolated from the Chinese medicinal herb, Qing-Dai or *Indigofera tinctoria* L. (Han, J. Traditional Chinese medicine and the search for new antineoplastic drugs. *J. Ethnopharmacol.* 1988; 24(1): 1-17).

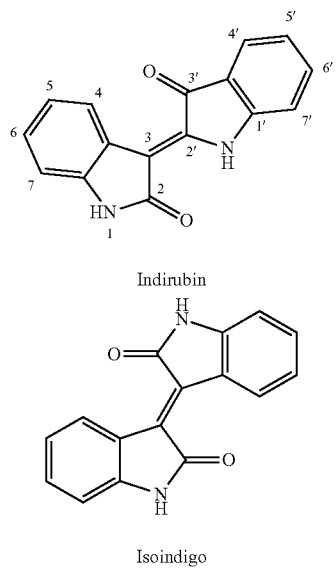

Indirubin

Isoindigo

Indirubin, isoindigo and numerous synthetic derivatives based on the bi-indole core structure have been shown to have very broad biological activities. Aza-indirubins and aza-isoindigos were synthesized by replacing a carbon or carbons with a nitrogen or nitrogens in the scaffolds of indirubin and isoindigo, respectively, and shown to have the biological activities similar to those of indirubins and isoindigos (Kritsanida, M. et al. Synthesis and antiproliferative activity of 7-azaindirubin-3'-oxime, a 7-aza isostere of the natural indirubin pharmacophore. *J. Nat. Prod.* 2009; 72(12): 2199-2202.; Wang, Z. et al. Synthesis and biological evaluation of 7-azaisoindigo derivatives. *Arch Pharm (Weinheim)* 2010; 343(3): 160-166.; Li X. et al. Anti-tumor effects in vitro and in vivo of novel 7-azaisoindigos. Chinese J. Cell Biol. 2013; 35(3): 334-340). The common feature of all these chemicals is that the two (aza)indoles are coupled to form structurally an extended pi-conjugated system. We believe that the similarity in three dimensional core structures of these compounds confers their similar biological functions, i.e., it is mainly the three dimensional structure, rather than just the chemical composition of the scaffold of these compounds, that is responsible for the biological activities. We hypothesized that modifying the chemical composition but maintaining such extended pi-conjugated system could result in new chemical entities with similar biological functions to those of indirubins and isoindigos. We, therefore, designed and synthesized two novel types of chemical entities, 1'-oxo-(aza)indirubins and 1'-oxo-(aza) isoindigos, by coupling (aza)indole with benzofuranone. Functional testing confirmed that, similar to indirubins and isoindigos, these novel molecules could also inhibit growth of tumor cells.

Natural products have always been a rich resource in drug discovery. Many important drugs, such as Aspirin, Digoxin, Paclitaxel, etc., were developed through understanding the biological activities and optimizing the chemical structures of natural products. A traditional Chinese medicinal receipe "Dang Gui Lu Hui Wan", which contains the herb "Qing Dai" or indigo naturalis, had been used for a long time in China to treat chronic myeloid leukemia (CML). The active molecular components of the recipe had not been known until the 1960s when Chinese scientists identified indirubin (Wu, L., Yang, Y. & Zhu, Z. Studies on the active principles of *indigofera tinctoria* in the treatment of CML. *Comm. Chinese Herb. Med.* 1979; 9(1): 6-8). Subsequent research in China on the structure activity relationship of indirubins and their isomers, isoindigos, resulted in the development of the novel anti-cancer drugs, indirubin and meisoindigo (Meisoindigo, or N-methyl-isoindigo) (Institute of Haematology, Chinese Academy of Medical Sciences. Clinical studies of Dang Gui Lu Hui Wan in the treatment of CML. *Chinese J. Intern. Med.*, 1979; 15: 86-88; Institute of Haematology, Chinese Academy of Medical Sciences. Clinical and experimental studies in the treatment of chronic granulocytic leukemia with indirubin. *Zhonghua Nei Ke Za Zhi* 1979; 18(2): 83-88; Wu, K., Zhang, M., Fang, Z. & Huang, L. Potential antileukemic agents, synthesis of derivatives of indirubin, indigo, and isoindigotin. *Yao Xue Xue Bao* 1985; 20(11): 821-826; Ji, X., Zhang, F., Liu, Y. & Gu, Q. Studies on the antineoplastic action of N-methylisoindigotin. *Yao Xue Xue Bao.* 1985; 20(4): 247-251). Indirubin and meisoindigo were the most effective anti-CML drugs in China before the targeted therapy drug, Imatinib Mesylate (Gleevec), was approved by the FDA in 2001. Due to different mechanisms of action (MOA), indirubin and meisoindigo can still be useful for Imatinib-resistant patients (Kim, W. et al. 5'-OH-5-nitro-Indirubin oxime (AGM130), an Indirubin derivative, induces apoptosis of Imatinib-resistant chronic myeloid leukemia cells. *Leuk. Res.* 2013; 37(4): 427-433).

The derivatives with a core structure similar to indirubin and isoindigo (hereafter collectively referred as "indirubins") have exhibited a wide range of biological activities through modulating functions of various proteins, such as enzymes and transcriptional factors that are critical for cell proliferation and differentiation, apoptosis, inflammation, angiogenesis, metabolism, etc. Different derivatives can have different selectivity and potency (Duensing, S. et al. Cyclin-dependent kinase inhibitor indirubin-3'-oxime selectively inhibits human papillomavirus type 16 E7-induced numerical centrosome anomalies. *Oncogene* 2004; 23(50): 8206-8215; Lee, J. et al. Induction of apoptosis by a novel indirubin-5-nitro-3'-monoxime, a CDK inhibitor, in human lung cancer cells. *Bioorg. Med. Chem. Lett.* 2005; 15(17): 3948-3952; Moon, M. et al. Synthesis and structure-activity relationships of novel indirubin derivatives as potent antiproliferative agents with CDK2 inhibitory activities. *Bioorg. Med. Chem.* 2006; 14(1): 237-246; Choi, S. et al. 5, 5'-substituted indirubin-3'-oxime derivatives as potent cyclin-dependent kinase inhibitors with anticancer activity. *J. Med. Chem.* 2010; 53(9): 3696-3706), and therefore can be effective in treating numerous different diseases by targeting various signaling pathways involved in the pathogeneses of the diseases.

Cyclin-dependent kinases (CDKs) are a family of serine/threonine protein kinases. The human genome contains 21 genes encoding CDKs and 5 other genes encoding CDK-like (CDKL) kinases (Malumbres, M. et al. Cyclin-dependent kinases: a family portrait. *Nat. Cell Biol.* 2009; 11(11): 1275-1276). Cyclins comprise a large family of proteins with diverse functions, each bound to its catalytic partner, CDK. By itself, CDKs exhibit little kinase activity. Cyclin bindings not only activate CDKs but also determine the substrates of the enzyme complexes. Sequential activation of CDKs and phosphorylation of key CDK substrates control each phase of cell cycle progression in all eukaryotes. Aberrant CDK activity leading to uncontrolled cell proliferation is a common feature of most cancer types (Sherr, C. Cancer cell cycles. *Science* 1996; 274(5293): 1672-1677). Targeting CDKs to arrest proliferation and induce apoptosis in neoplastic cells has been a promising strategy to treat cancer (Abate, A., Pentimalli, F., Esposito, L. & Giordano, A. ATP-noncompetitive CDK inhibitors for cancer therapy: an overview. *Expert Opin. Investig. Drugs* 2013; 22(7): 895-906). More than 10 small molecule CDK inhibitors with different chemical scaffolds have been tested in clinical trials over the past decade, however, none of them has been approved (Jorda, R., Paruch, K. & Krystof, V. Cyclin-dependent kinase inhibitors inspired by roscovitine: purine bioisosteres. *Curr. Pharm. Des.* 2012; 18(20): 2974-2980; Bose, P., Simmons, G. & Grant, S. Cyclin-dependent kinase inhibitor therapy for hematologic malignancies. *Expert. Opin. Investig. Drugs* 2013; 22(6): 723-738; Galons, H., Oumata, N., Gloulou, O. & Meijer, L. Cyclin-dependent kinase inhibitors closer to market launch?. *Expert. Opin. Ther. Pat.* 2013; 23(8): 945-963). One of the challenges that the CDK-targeted therapy faces is that the disruption of a CDK-mediated pathway has potentially serious consequences. Modest therapeutic effects are usually accompanied by severe side effects. The toxicity of a CDK inhibitor, depending on its potency, selectivity, and ATP-competitivity or non-competitivity, could be restricted in certain cell types or more general (Malumbres, M., Pevarello, P., Barbacid, M. & Bischoff, J. CDK inhibitors in cancer therapy: what is next?. *Trends Pharmacol. Sci.* 2008; 29(1): 16-21; Abate, A., Pentimalli, F., Esposito, L. & Giordano, A. ATP-noncompetitive CDK inhibitors for cancer therapy: an overview. *Expert Opin. Investig. Drugs* 2013; 22(7): 895-906).

Indirubin and its isoform derivative, meisoindigo, have shown antitumor activities with relatively low toxicities in treating leukemia in China. Indirubin acts as a potent CDK inhibitor by interacting with the ATP-binding site of CDK2 through van der Waals interactions and three hydrogen bonds (Hoesse, R. et al. Indirubin, the active constituent of a Chinese antileukaemia medicine, inhibits cyclin-dependent kinases. *Nat. Cell Biol.* 1999; 1(1): 60-67). An indirubin derivative, indirubin-3'-monoxime inhibits the proliferation of various types of cells, mainly through arresting the cells in the G2/M phase of the cell cycle. Structural modifications can confer indirubin derivatives with different potencies and selectivities to different subtypes of CDKs. The unique properties of indirubins suggest their great therapeutic potential in the treatment of diseases with aberrant cell proliferation, such as various types of tumors (Eisenbrand, G., Hippe, F. & Jakobs, S. Molecular mechanisms of indirubin and its derivatives: novel anticancer molecules with their origin in traditional Chinese phytomedicine. *J. Cancer Res. Clin. Oncol.*, 2004; 130: 627-635).

In addition to CDKs, the activities of other protein kinases, such as glycogen synthase kinase-3 (GSK3) can also be modulated by indirubins. GSK3 was first discovered for its ability to phosphorylate glycogen synthase (GS) and to consequently reduce GS activity. GSK3 is also able to phosphorylate other proteins in glucose metabolic pathways, such as signal transduction protein (insulin receptor substrate 1, IRS1), glycolytic enzyme (glucose 6-phosphatase, G6Pase) and gluconeogenic enzyme (phosphoenolpyruvate carboxykinase, PEPCK). Beyond the roles in glucose metabolism, GSK3 is involved in many signal transduction pathways related to innate as well as acquired or adaptive immune responses (Wang, H., Brown, J. & Martin, M. Glycogen synthase kinase 3: a point of convergence for the host inflammatory response. *Cytokine* 2011; 53(2): 130-140). GSK3 is also one of the key enzymes in neuronal development and regeneration (Seira, O. & Del Rio, J. Glycogen Synthase Kinase 3 Beta (GSK3β) at the Tip of Neuronal Development and Regeneration. *Mol. Neurobiol. Mol. Neurobiol.* 2014; 49(2): 931-44). Aberrant activity of GSK3 is correlated with degeneration of neuronal cells and the deposit of amyloid β (Aβ) in the brain and is able to directly accelerate the process of Aβ formation and tau protein over-phosphorylation, which is the cause of neurofibrillary tangles. Moreover, inhibition of GSK3 activity was found to be a mechanism through which certain antipsychotic drugs work (Jope, R., Yuskaitis, C. & Beurel, E. Glycogen Synthase Kinase-3 (GSK3): Inflammation, Diseases, and Therapeutics. *Neurochem Res.* 2007; 32(4-5): 577-595). Targeting GSK3, therefore, can have very broad therapeutic applications (Maes, M. et al. New drug targets in depression: inflammatory, cell-mediated immune, oxidative and nitrosative stress, mitochondrial, antioxidant, and neuroprogressive pathways. And new drug candidates—Nrf2 activators and GSK-3 inhibitors. *Inflammopharmacology* 2012; 20(3): 127-150). It can be used to treat disorders of glucose metabolism (Gao, C., Hölscher, C., Liu, Y. & Li, L. GSK3: a key target for the development of novel treatments for type 2 diabetes mellitus and Alzheimer disease. *Rev. Neurosci.* 2011; 23(1): 1-11), such as type 2 diabetes (T2D); inflammatory and autoimmune diseases (Beurel, E., Michalek, S. & Jope, R. Innate and adaptive immune responses regulated by glycogen synthase kinase-3 (GSK3). *Trends Immunol.* 2010; 31(1): 24-31), such as arthritis; neurodegenerations (Ma, T. GSK3 in Alzheimer's Disease: Mind the Isoforms. *J. Alzheimers Dis.* 2014; 39(4): 707-710), such as Alzheimer's; and psychoses (Cole, A. Glycogen synthase kinase 3 substrates in mood disorders and schizophrenia. *FEBS J.* 2013; 280(21): 5213-5227), such as schizophrenia, etc. Indirubin is the first type of compound shown to inhibit GSK3 activities at lower nanomolar concentrations (Leclerc, S. et al. Indirubins inhibit glycogen synthase kinase-3 beta and CDK5/p25, two protein kinases involved in abnormal tau phosphorylation in Alzheimer's disease. A property common to most cyclin-dependent kinase inhibitors?. *J. Biol. Chem.* 2001; 276(1): 251-256). Indirubins can, therefore, be used to treat various types of diseases as described above.

Not limited to protein kinases, indirubins are also able to modulate activities of other key components in signal transduction pathways, and therefore affect cell proliferation and differentiation at different stages. Signal transducer and activator of transcription (STAT) is a family of transcriptional factors important in many cellular processes, and plays key roles in immune response, host defense, hematopoiesis, angiogenesis, metabolism, oncogenesis, etc. (O'Shea, J., Holland, S. & Staudt, L. JAKs and STATs in immunity, immunodeficiency, and cancer. *N. Engl. J. Med.* 2013; 368(2): 161-170). Janus kinase-STAT (JAK-STAT), originally identified as the signaling cascade downstream of cytokine receptors, provides a direct pathway to translate extracellular signals from a variety of ligands including cytokines, hormones and growth factors, etc., into a transcriptional response. Activated STATs binding to specific regulatory DNA sequences activate or repress the transcription of their target genes. Among the 7 members of the STAT family, STAT3 is indispensable in the differentiation and the activation of Th17, a type of T-helper cell critically involved in autoimmune diseases and tumors (Chaudhry, A. et al. CD4+ regulatory T cells control TH17 responses in a Stat3-dependent manner. *Science* 2009; 326(5955): 986-991; Camporeale, A. & Poli, V. IL-6, IL-17 and STAT3: a holy trinity in auto-immunity?. *Front Biosci (Landmark Ed)* 2012; 17: 2306-2326). Imbalance of Th17 and regulatory T cells (Treg) is the major cause of many inflammatory and autoimmune disorders. Targeting STAT3 therefore holds great promise for developing drugs with very broad indications (Mankan, A. & Greten, F. Inhibiting signal transducer and activator of transcription 3: rationality and rationale design of inhibitors. *Expert Opin. Investig. Drugs* 2011; 20(9): 1263-1275). Potent and selective STAT3 inhibitors can be effective therapeutics not only for different tumors (Page, B., Ball, D. & Gunning, P. Signal transducer and activator of transcription 3 inhibitors: a patent review. *Expert. Opin. Ther. Pat.* 2011; 21(1): 65-83.; Wang, X., Crowe, P., Goldstein, D. & Yang, J. STAT3 inhibition, a novel approach to enhancing targeted therapy in human cancers (review). *Int. J. Oncol.* 2012; 41(4): 1181-1191), but also for various other inflammatory or immune-related diseases in which STAT3 or Th17 is involved (Ghoreschi, K. et al. T helper 17 cell heterogeneity and pathogenicity in autoimmune disease. *Trends Immunol.* 2011; 32(9): 395-401), such as rheumatoid arthritis (Ju, J. et al. Modulation of STAT-3 in rheumatoid synovial T cells suppresses Th17 differentiation and increases the proportion of Treg cells. *Arthritis Rheum.* 2012; 64(11): 3543-3552), inflammatory bowel diseases (IBD) (Li, Y., de Haar, C., Peppelenbosch, M. & van der Woude, C. New insights into the role of STAT3 in IBD. *Inflamm Bowel Dis.* 2012; 18(6): 1177-1183), dermatitis and psoriasis (Kim, M. et al. Indirubin, a purple 3,2-bisindole, inhibited allergic contact dermatitis via regulating T helper (Th)-mediated immune system in DNCB-induced model. *J. Ethnopharmacol.* 2013; 145(1): 214-219.; Novelli, L., Chimenti, M., Chiricozzi, A. & Perricone, R. The new era for the treatment of psoriasis and psoriatic arthritis: perspectives and validated strategies. *Autoimmun Rev.* 2014; 13(1): 64-69), systemic lupus erythematosus (SLE) (Nalbandian, A., Crispin, J. & Tsokos, G. Interleukin-17 and systemic lupus erythematosus: current concepts. *Clin. Exp. Immunol.* 2009; 157(2): 209-215), type 1 diabetes (T1D) (Shao, S. et al. Th17 cells in type 1 diabetes. *Cell Immunol.* 2012; 280(1): 16-21), restenosis (Schwaiberger, A. et al. Indirubin-3'-monoxime blocks vascular smooth muscle cell proliferation by inhibition of signal transducer and activator of transcription 3 signaling and reduces neointima formation in vivo. *Arterioscler. Thromb. Vasc. Biol.* 2010; 30(12): 2475-2481), etc.

Indirubins can inhibit STAT3 signaling (Nam, S. et al. Indirubin derivatives inhibit Stat3 signaling and induce apoptosis in human cancer cells. *Proc. Natl. Acad. Sci. U.S.A.* 2005; 102(17): 5998-6003), prevent STAT3 from being activated (Aggarwal, B. et al. Targeting signal-transducer-and-activator-of-transcription-3 for prevention and therapy of cancer: modern target but ancient solution. *Ann. N. Y. Acad. Sci.* 2006; 1091: 151-169), block tumor angiogenesis (Zhang, X. et al. Indirubin inhibits tumor growth by antitumor angiogenesis via blocking VEGFR2-mediated JAK/STAT3 signaling in endothelial cell. *Int. J. Cancer* 2011; 129(10): 2502-2511.), induce cancer cell apoptosis (Ribas, J. et al. 7-Bromoindirubin-3'-oxime induces caspase-independent cell death. *Oncogene* 2006; 25(47): 6304-6318), inhibit Th17 cell differentiation (Glatigny S, et al. Treatment of collagen-induced arthritis by Natura-alpha via regulation of Th-1/Th-17 responses. *Eur. J. Immunol.* 2010. 40(2): 460-469), etc. Both the mechanism of action and the experimental evidence indicate that indirubins can be utilized to treat a number of diseases as described above, including but not limited to, different types of tumors and various inflammatory and autoimmune diseases.

The broad biological activities of indirubins have also been observed through their regulatory effects on multiple signaling transduction pathways, numerous cytokines and different types of cells. Indirubins can induce neutrophil production while suppressing Th17 cell differentiation (Suzuki, K. et al. Indirubin, a Chinese anti-leukaemia drug, promotes neutrophilic differentiation of human myelocytic leukaemia HL-60 cells. *Br. J. Haematol.* 2005; 130(5): 681-190); inhibit the maturation of monocyte-derived dendritic cells (Vlachos, C. et al. Malassezia-derived indoles activate the aryl hydrocarbon receptor and inhibit Toll-like receptor-induced maturation in monocyte-derived dendritic cells. *Br. J. Dermatol.* 2012; 167(3): 496-505.); modulate the functions of macrophages (Babcock, A., Anderson, A. & Rice, C. Indirubin-3'-(2,3 dihydroxypropyl)-oximether (E804) is a potent modulator of LPS-stimulated macrophage functions. *Toxicol. Appl. Pharmacol.* 2013; 266(1): 157-166); block smooth muscle cell proliferation (Schwaiberger, A. et al. Indirubin-3'-monoxime blocks vascular smooth muscle cell proliferation by inhibition of signal transducer and activator of transcription 3 signaling and reduces neointima formation in vivo. *Arterioscler. Thromb. Vasc. Biol.* 2010; 30(12): 2475-2481); increase neurogenesis of human neural progenitor cells (Lange, C. et al. Small molecule GSK-3 inhibitors increase neurogenesis of human neural progenitor cells. *Neurosci. Lett.* 2011; 488(1): 36-40.; Castelo-Branco, G., Rawal, N. & Arenas, E. GSK-3beta inhibition/beta-catenin stabilization in ventral midbrain precursors increases differentiation into dopamine neurons. *J. Cell Sci.* 2004; 117(Pt 24): 5731-5737); decrease adipocyte cell differentiation (Choi, O. et al. The small molecule indirubin-3'-oxime activates Wnt/β-catenin signaling and inhibits adipocyte differentiation and obesity. *Int. J. Obes (Lond).* 2013; 209: 1-9); impair mitochondria functions (Varela, A. et al. Indirubin-3'-oxime impairs mitochondrial oxidative phosphorylation and prevents mitochondrial permeability transition induction. *Toxicol. Appl. Pharmacol.*

2008; 233(2): 179-185); inhibit production of inflammatory cytokines (Kunikata, T. et al. Indirubin inhibits inflammatory reactions in delayed-type hypersensitivity. *Eur. J. Pharmacol.* 2000; 410(1): 93-100.; Glatigny S, et al. Treatment of collagen-induced arthritis by Natura-alpha via regulation of Th-1/Th-17 responses. *Eur. J. Immunol.* 2010. 40(2): 460-469); etc. In addition to the JAK/STAT pathway, other signaling transduction pathways on which indirubins have shown effects include the NFκB and JNK pathways (Kim, J. & Park, G. Indirubin-3-monoxime exhibits anti-inflammatory properties by down-regulating NF-κB and JNK signaling pathways in lipopolysaccharide-treated RAW264.7 cells. *Inflamm. Res.* 2012; 61(4): 319-325); the Wnt/β-Catenin pathway (Zahoor, M., Cha, P., Min, D. & Choi, K. Indirubin-3'-Oxime Reverses Bone Loss in Ovariectomized, Hindlimb-Unloaded Mice via Activation of the Wnt/β-Catenin Signaling. *J. Bone Miner Res.* 2014; 29(5): 1196-1205); the aryl hydrocarbon receptor (AHR) pathway (Stevens, E., Mezrich, J. & Bradfield, C. The aryl hydrocarbon receptor: a perspective on potential roles in the immune system. *Immunology* 2009; 127(3): 299-311); etc. Different indirubin derivatives with different selectivities, therefore, can further be used for the treatments of diseases with different etiopathogeneses, such as cardiovascular diseases (Schwaiberger, A. et al. Indirubin-3'-monoxime blocks vascular smooth muscle cell proliferation by inhibition of signal transducer and activator of transcription 3 signaling and reduces neointima formation in vivo. *Arterioscler. Thromb. Vasc. Biol.* 2010; 30(12): 2475-2481), obesity (Choi, O. et al. The small molecule indirubin-3'-oxime activates Wnt/β-catenin signaling and inhibits adipocyte differentiation and obesity. *Int. J. Obes* (*Lond*). 2013; 209: 1-9), osteoporosis (Zahoor, M., Cha, P., Min, D. & Choi, K. Indirubin-3'-Oxime Reverses Bone Loss in Ovariectomized, Hindlimb-Unloaded Mice via Activation of the Wnt/β-Catenin Signaling. *J. Bone Miner Res.* 2014; 29(5): 1196-1205), asthma (Gupta, S., Sundaram, C., Reuter, S. & Aggarwal, B. Inhibiting NF-κB activation by small molecules as a therapeutic strategy. Biochim *Biophys Acta* 2010; 1799 (10-12): 775-787.; Mak, N K. et al. Inhibition of RANTES expression by indirubin in influenza virus-infected human bronchial epithelial cells. *Biochem Pharmacol.* 2004; 67(1): 167-74), aging (Spindler, S. et al. Novel protein kinase signaling systems regulating lifespan identified by small molecule library screening using drosophila. 2012; *PLoS One*, 7(2): e29782), graft-vs-host disease (GVHD) (Stevens, E., Mezrich, J. & Bradfield, C. The aryl hydrocarbon receptor: a perspective on potential roles in the immune system. *Immunology* 2009; 127(3): 299-311), and viral infections including encephalitis, AIDS, etc. (Chang, S. et al. Antiviral activity of isatis indigotica extract and its derived indirubin against Japanese encephalitis virus. *Evid Based Complement Alternat Med.* 2012; 2012(925830): 1-7; Heredia, A. et al. Indirubin 3'-onoxime, from a Chinese traditional herbal formula, suppresses viremia in humanized mice infected with multidrug-resistant HIV. *AIDS Res. Hum. Retroviruses* 2014; 30(5): 403-406).

As described above, indirubins can inhibit activation of different kinases and various signaling transduction pathways that are critically involved in the pathogeneses of numerous diseases. Their broad activities and mild toxicities make indirubins promising candidates for drug development. Their poor solubility in water and in lipid, however, has been one of the hurdles that have prevented them from being successful drugs. Many efforts have been devoted to modifying indirubins for better potency, specificity and bioavailability, but with only limited success. It is, therefore, necessary to develop new types of chemical entities with biological activities similar to those of indirubins, but with more desirable druggable properties.

CONTENT OF THE INVENTION

The purpose of the present invention is to provide designs for the new types of chemical entities, 1'-oxo-(aza)indirubins (formula I) and 1'-oxo-(aza)isoindigos (formula II) or their pharmaceutically acceptable salts, of which the three dimensional structures and biological functions are similar to those of indirubins and isoindigos. Advantages of these compounds include a stronger biological activity, an improved solubility, etc.

Another purpose of the present invention is to provide preparation methods, pharmaceutical compositions and uses of the described compounds.

The invented new chemical entities (formula I and II) are formed by coupling one moiety of indole (or azaindole) with another moiety of benzofuranone, resulting in a derivative of heterocyclic rings with an extended pi-conjugated system similar to that of bi-indole derivatives. Compared with indirubins and isoindigos, these new chemical entities or the pharmaceutically acceptable salts thereof have the advantages of retained or increased biological activities, improved solubility, etc.

Formula I

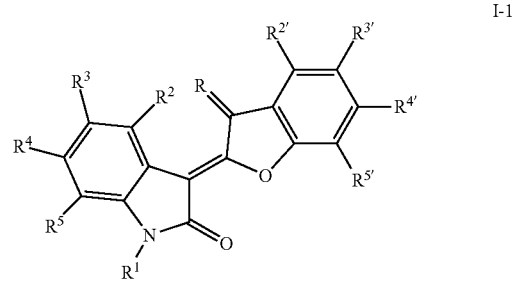

I-1

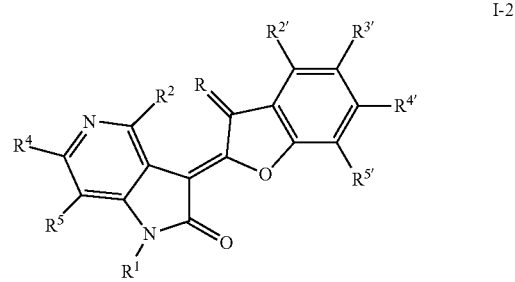

I-2

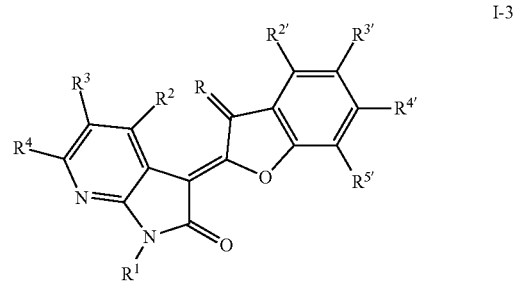

I-3

Formula II

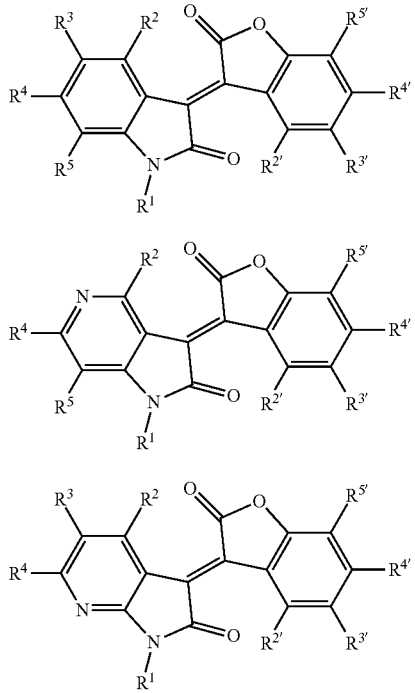

In the above 1'-oxo-(aza)indirubins (I-1~3) and 1'-oxo-(aza)isoindigos (II-1~3) or their pharmaceutically acceptable salts, $R^1$ represents H or D, the following groups that may be unsubstituted or substituted by 1 to 3 substituents: $C_1$~$C_6$ alkyl, aryl, aralkyl, acyl, aroyl, glycosyl or biosyl protected by acyl, glycosyl or biosyl; wherein said substituents are selected from: halogen, hydroxyl, $C_1$-$C_3$ alkyl, nitro or amino;

$R^2$, $R^3$, $R^4$, $R^5$, $R^{2'}$, $R^{3'}$, $R^{4'}$ and $R^{5'}$ independently represent H, D, halogen, hydroxyl, sulfhydryl, $C_1$~$C_4$ alkyl, nitro, amino, amido, amide, or the following groups that may be unsubstituted or substituted by 1 to 3 substituents: $C_1$~$C_4$ alkoxyl, methylthio, phenyl, phenoxyl, aryl, aralkyl, trifluoromethyl, acyl, aroyl, sulfonyl, sulfamoyl, isocyanate, or alkyl isocyanate; wherein said substituents are selected from: halogen, hydroxyl, $C_1$~$C_3$ alkyl, nitro or amino;

R represents oxygen, sulfur, selenium, or a $NR^6$ or $NOR^6$ group, wherein $R^6$ is H, or the following groups that may be unsubstituted or substituted by 1 to 3 substituents: $C_1$~$C_6$ straight-chain or branched-chain alkyl, aryl, aralkyl, $C_3$~$C_6$ alicyclic group, acyl, aroyl, sulfonyl or phosphoryl; wherein said substituents are selected from: halogen, hydroxyl, $C_1$~$C_3$ alkyl, nitro or amino.

Isatin (Indole-2,3-dione) derivatives have anti-viral, anti-bacterial and anti-cancer activities (Vine, K. et al. Cytotoxic and anticancer activities of isatin and its derivatives: a comprehensive review from 2000-2008. *Anticancer Agents Med Chem.* 2009; 9(4): 397-414.; Aboul-Fadl, T. et al. Schiff bases of indoline-2,3-dione (isatin) with potential antiproliferative activity. *Chem. Cent. J.* 2012; 6(1): 49-59). Benzofuranone derivatives are analogues of flavonoids, and have shown strong inhibitory effects on CDKs and on tumor growth (Schoepfer, J. et al. Structure-based design and synthesis of 2-benzylidene-benzofuran-3-ones as flavopiridol mimics. *J. Med. Chem.* 2002; 45(9): 1741-1747). 1'-oxo-(aza)indirubins and 1'-oxo-(aza)isoindigos that are formed by coupling isatin and benzofuranone, therefore, should also have those activities. In addition, the alkalescency of the pyridine ring in azaindole makes the coupled molecules more easily form salts or prodrugs with acids or acidic substances. The new chemical entities described in the present invention have, therefore, an improved solubility or/and bioavailability that are critical for druggability of small molecule compounds.

The novel chemical entities described in the present invention are 1'-oxo-(aza)indirubins (I-1~3) and 1'-oxo-(aza)isoindigos (II-1~3) or their pharmaceutically acceptable salts, which are formed by coupling a moiety of benzofuranones with another moiety of indoles or azaindoles, wherein, (I-1) represents 1'-oxo-indirubin derivatives; (I-2) represents 1'-oxo-5-azaindirubin derivatives; (I-3) represents 1'-oxo-7-azaindirubin derivatives; (II-1) represents 1'-oxo-isoindigo derivatives; (II-2) represents 1'-oxo-5-azaisoindigo derivatives; and (II-3) represents 1'-oxo-7azaisoindigo derivatives. In a preferred embodiment, $R^1$ represents H, D, $C_1$-$C_6$ alkyl, aryl, aralkyl, acyl, aroyl, glycosyl protected by acyl, glycosyl;

$R^2$, $R^3$, $R^4$, $R^5$, $R^{2'}$, $R^{3'}$, $R^{4'}$ and $R^{5'}$ independently represent H, halogen, hydroxyl, sulfhydryl, $C_1$~$C_4$ alkyl, nitro, amino, amido, amide, $C_1$~$C_4$ alkoxy, methylthio, phenyl, phenoxy, aryl, aralkyl, trifluoromethyl, acyl, aroyl, sulfonyl, sulfamoyl, isocyanate;

The glycosyl described above is arabinose, xylose, ribose, mannose, or glucose;

R represents oxygen, sulfur, selenium, or a $NR^6$ or $NOR^6$ group, wherein $R^6$ is H, $C_1$~$C_6$ straight-chain or branched-chain, alkyl, aryl, aralkyl, $C_3$~$C_6$ alicyclic group, acyl, aroyl, sulfonyl or phosphoryl.

The novel chemical entities described in the present invention are 1'-oxo-(aza)indirubin derivatives and 1'-oxo-(aza)isoindigo derivatives, including their enantiomers, racemates, cis-trans isomers and any combinations, or their pharmaceutically acceptable salts, wherein, in another preferred embodiment, the said compounds are selected from 1'-oxo-indirubin derivatives (I-1): the compounds No. 1~60 as listed in Table 1; from 1'-oxo-5-azaindirubin derivatives (I-2): the compounds No. 61~74 as listed in Table 2; from 1'-oxo-7-azaindirubin derivatives (I-3): the compounds No. 75~90 as listed in Table 3; from 1'-oxo-isoindigo derivatives (II-1): the compounds No. 90~420 as listed in Table 4; from 1'-oxo-5-azaisoindigo derivatives (II-2): the compounds No. 121~435 as listed in Table 5; from 1'-oxo-7azaisoindigo derivatives (II-3): the compounds No. 136~453 as listed in Table 6.

The pharmaceutically acceptable salts described in the present invention are the salts of 1'-oxo-indirubin derivatives (I-1~3) and 1'-oxo-isoindigo derivatives (II-1~3), wherein, in another preferred embodiment, the said pharmaceutically acceptable salts are selected from the salts formed with inorganic acids or organic acids. The said inorganic acids include, but are not limited to: hydrochloric acid, hydrobromic acid, phosphoric acid, nitric acid, and sulfuric acid; the said organic acids include but are not limited to: methanoic acid, acetic acid, propionic acid, succinic acid, naphthalene disulfonic acid (1, 5), asiatic acid, carbenoxolone, glycyrrhetinic acid, tartaric acid, oleanolic acid, crataegolic acid, ursolic acid, corosolic acid, betulinic acid, boswellic acid, oxalic acid, lactic acid, salicylic acid, benzoic acid, butylcarboxylic acid, diethylacetic acid, malonic acid, amber acid, fumaric acid, pimelic acid, hexanedioic acid, maleic acid, malic acid, aminosulfonic acid, phenylpropionic acid, gluconic acid, ascorbic acid, nicotinic acid, isonicotinic acid, methanesulfonic acid, ethanesulfonic acid, para-toluenesulfonic acid, citric acid and amino acid.

The present invention provides methods for preparing pharmaceutical compositions comprising (a) the compound of 1'-oxo-indirubin derivatives (I-1~3) or/and 1'-oxo-isoindigo derivatives (II-1~3), including their enantiomers, racemates, cis-trans isomers and any combinations, or the pharmaceutically acceptable salts thereof, mixed with (b) pharmaceutically acceptable carriers, thereby forming the pharmaceutical compositions.

In another preferred embodiment, the formulations and the dosage forms of a pharmaceutical composition prepared with 1'-oxo-indirubin derivatives (I-1~3) or/and 1'-oxo-isoindigo derivatives (II-1~3) including their enantiomers, racemates, cis-trans isomers and any combinations, or the pharmaceutically acceptable salts thereof described in the present invention include, but are not limited to: low capacity injection, medium capacity injection, high capacity injection, dried powder injection, emulsion for injection, tablet, pill, capsule, paste, cream, patch, liniment, powder, spray, implant, drop, suppository, ointment; various nano preparations; or liposomes, which can be made into injections as described above.

The present invention provides a use of 1'-oxo-(aza) indirubin derivatives (I-1~3) and 1'-oxo-(aza)isoindigo derivatives (II-1~3), including their enantiomers, racemates, cis-trans isomers and any combinations, pharmaceutically acceptable salts thereof, and pharmaceutical compositions thereof in treating the following diseases: the diseases related to abnormal activities of cyclin-dependent kinases, including but not limited to various types of cancer; the diseases related to abnormal activities of glycogen synthase kinase-3, including but not limited to disturbance of carbohydrate metabolism, inflammatory and autoimmune diseases, neurodegeneration diseases, and mental disorders; the diseases related to abnormal JAK-STAT signal transduction pathway or an abnormal component of the JAK-STAT pathway, including but not limited to various types of cancer, inflammatory and autoimmune diseases; the diseases related to abnormalities of cell differentiation or self-defense system, including but not limited to various types of cancer, inflammatory and autoimmune diseases, cardiovascular disorders, obesity, osteoporosis, and viral infections.

The present invention provides a use of 1'-oxo-(aza) indirubin derivatives (I-1~3) and 1'-oxo-(aza)isoindigo derivatives (II-1~3), including their enantiomers, racemates, cis-trans isomers and any combinations, pharmaceutically acceptable salts thereof, and pharmaceutical compositions thereof as CDK (cyclin dependent kinase) inhibitors.

The present invention provides a use of 1'-oxo-(aza) indirubin derivatives (I-1~3) and 1'-oxo-(aza)isoindigo derivatives (II-1~3), including their enantiomers, racemates, cis-trans isomers and any combinations, pharmaceutically acceptable salts thereof, and pharmaceutical compositions thereof as GSK3 (glycogen synthase kinase) inhibitors.

The present invention provides a use of 1'-oxo-(aza) indirubin derivatives (I-1~3) and 1'-oxo-(aza)isoindigo derivatives (II-1~3), including their enantiomers, racemates, cis-trans isomers and any combinations, pharmaceutically acceptable salts thereof, and pharmaceutical compositions thereof as STATs (signal transducer and activator of transcription) inhibitors.

The present invention provides a use of 1'-oxo-(aza) indirubin derivatives (I-1~3) and 1'-oxo-(aza)isoindigo derivatives (II-1~3), including their enantiomers, racemates, cis-trans isomers and any combinations, pharmaceutically acceptable salts thereof, and pharmaceutical compositions thereof as modulators of cellular neogenesis and differentiation.

The present invention provides a combination use of 1'-oxo-(aza)indirubin derivatives (I-1~3) and 1'-oxo-(aza) isoindigo derivatives (II-1~3), including their enantiomers, racemates, cis-trans isomers and any combinations, pharmaceutically acceptable salts thereof, and pharmaceutical compositions thereof in treating or/and preventing disorders, including but not limited to glucose metabolism disorders, inflammatory and autoimmune disorders, cell proliferation disorders, neurodegeneration and mental disorders, cardiovascular diseases, obesity, osteoporosis, and viral infections. The said combination can be single, double or multiple agents; simultaneous or sequential administrations; with or without other therapies that include but are not limited to radiotherapy, Chinese herb medicine or alterative medicine, surgery, biological modulators and gene therapy.

In a preferred embodiment, the compounds represented by the general formula (I) and (II) are listed in the following tables 1~6, which are the examples of 1'-oxo-indirubin derivatives (I-1~3) and 1'-oxo-isoindigo derivatives (II-1~3) that have been synthesized.

| Compound No. | Type |
| --- | --- |
| 1-60 | 1'-oxo-indirubins (I-1) |
| 61-74 | 1'-oxo-5-azaindirubins (I-2) |
| 75-90 | 1'-oxo-7-azaindirubins (I-3) |
| 91-120 | 1'-oxo-isoindigos (II-1) |
| 121-135 | 1'-oxo-5-azaisoindigos (II-2) |
| 136-153 | 1'-oxo-7-azaisoindigos (II-3) |

All the newly synthesized compounds have been characterized via various physico-chemical methods, including $^1$H-NMR, ESI-MS or HRMS and elemental analysis, etc.

Administration and Delivery

Usually, the compound(s) or/and the composition(s) described in the present invention are administered at effective doses in treating the described corresponding diseases. The compounds described in the present invention can be delivered through any suitable route in a form that is appropriate for the said route and at a dose that is expected to be effective.

An effective dose of the compound(s) or/and the composition(s) needed for treating medical disorders can readily be determined by health care professionals using conventional preclinical or clinical methods.

In a preferred embodiment, the compound(s) or/and the composition(s) described in the present invention can be orally administered. Oral administration includes swallowing which delivers the compounds into the gastrointestinal tract, and sublingual administration which delivers the compounds directly into the blood through oral mucosa.

In another preferred embodiment, the compound(s) or/and the composition(s) described in the present invention can be administered directly into the blood, the muscle or the internal organs. The delivery routes in addition to gastrointestinal tract routes include but are not limited to intravenous, intra-arterial, intraperitoneal, intramural, intracardiac, intrauterine, intrathoracic, intracranial, intramuscular, and subcutaneous. The delivery devices include needle (including micro-needle) syringes, needleless syringes and infusion techniques.

In another preferred embodiment, the compound(s) or/and the composition(s) described in the present invention can be administered topically, i.e., applied locally onto the skin or mucosa, through the nose or intranasal, via intrarectal or intravaginal, par intraocular or intraauricular.

A treatment regimen with the compound(s) or/and the composition(s) described in the present invention is based on multiple considerations, which include patient's sex, age, weight; type of the disease; severity of the disease; drug administration route; and activity of specific compound applied. Therefore, treatment regimens can vary dramatically. Dose levels ranging from about 0.01 mg to about 1000 mg/kg/day can be used for the diseases described above. In a preferred embodiment, total daily dose (single dose× frequency) of the compound described in the present invention usually ranges from about 0.1 to about 500 mg/kg (mg weight of the compound/kg body weight); in another preferred embodiment, total daily dose of the compounds described in the present invention usually ranges from about 0.1 to about 300 mg/kg, or 0.5 mg to 200 mg, or 0.1 mg/kg to 10 mg/kg, or 0.1 mg/kg to 1.0 mg/kg. Each ingredient of the drug composition can contain such quantity, or portions of such quantity that constitute(s) the daily dose. In many cases, the compounds are administered multiple times per day (usually no more than 4 times). If necessary, multiple doses per day can usually be used to increase the total daily dose.

For oral administration, the compound(s) or/and the composition(s) described in the present invention can be provided as a tablet containing effective ingredient(s) of 0.01, 0.05, 0.1, 0.5, 1.0, 2.5, 5.0, 10.0, 15.0, 25.0, 75.0, 100, 125, 150, 175, 200, 250, or 500 mg, in order to adjust the dosage for individual patients according their symptoms. The formulated drug usually contains the effective ingredient of about 0.01 mg to about 500 mg, or in another preferred embodiment, of about 1 mg to about 100 mg. In the case of infusion at a constant rate, intravenous doses can range from about 0.01 to about 10 mg/kg/minute.

Based on the present invention, the suitable test subjects include mammals. Based on the present invention, the mammals include but are not limited to dog, cat, cattle, goat, sheep, horse, pig, rodents, lagomorphs, primates, etc., as well as the mammals in the uterus. In a preferred embodiment, human is a suitable test subject. The human test subject can be of any sex at any stage of the development. In another preferred embodiment, the present invention includes applications of one or multiple compounds described in the present invention for producing the pharmaceutical compositions for treatment of the diseases as described in the present invention.

Pharmaceutical Composition

The compounds themselves described in the present invention can be used in the pharmaceutical compositions treating diseases described in the present invention. In a preferred embodiment, pharmaceutically acceptable salts of these compounds better fit the need for medical applications, because an improved water solubility is conferred to these compounds by forming salts.

In another preferred embodiment, the present invention includes pharmaceutical compositions. The pharmaceutical compositions contain the invented compound(s) and pharmaceutical carriers. The said carriers can be solid, liquid or both, and can be prepared with the described compound(s) as dosage unit, such as tablet, in which 0.05% to 95% of the weight is the active compound(s). The invented compound(s) can couple with appropriate polymers that have properties of the carriers for targeted drugs, and can allow a presence of other pharmacologically active substances.

The compounds described in this invention can be administered via any route, preferably a route that is adequate for the formulation of a composition and for the dose level expected to use in the treatment. Active compounds and compositions can be administered, for example, orally, via rectum, non-gastrointestinal routes, or locally.

The orally administered solid form of a composition can be presented as single units, such as capsule (soft or hard); wafer capsule, lozenge, pill, or tablet, where each of the units contains at least one invented compound of a predetermined amount. In another preferred embodiment, oral dosage form can be powder, granules, or lozenge for sublingual. In these types of solid dosage forms, the invented compound is usually combined with one or more adjuvants. This type of capsule or tablet contains controlled release formulations. In the case of capsules, pills and tablets, the formulation may contain buffers or come with an enteric coating.

In another preferred embodiment, the orally administered drug composition can be a liquid dosage form. The liquid formulation, prepared with inactive diluent commonly used in the field (e.g., water), includes pharmaceutically acceptable cream, solution, suspension, syrup and elixir. This type of compositions can also contain adjuvants, such as moisturizer, emulsifier, suspending agent, flavoring agent (e.g., sweetener), and/or aromatizer.

In another preferred embodiment, the present invention includes non-gastrointestinal dosage forms. "Non-gastrointestinal administration" includes, for example, subcutaneous injection, intravenous injection, intraperitoneal injection, intramuscular injection, intrathoracic injection and infusion. The injectable preparations (e.g., sterile aqueous or oily preparation) can be made, by currently available technology, with dispersant, moisturizer, and/or suspending agent.

In another preferred embodiment, the present invention includes topical dosage forms. "Topical application" includes percutaneous (e.g., transdermal patch, or ionotherapy device), intraocular, intranasal, or inhalation. The compositions for topical administration also include, for example, gel, spray, ointment and cream. The topical formulations can include substances that enhance absorption or penetration of effective components via the skin or other affected areas. In the case that the invented compounds are applied through percutaneous devices, the delivery can be aided by a reservoir and patches with porous membranes or with a solid matrix. The typical formulations for this purpose include gel, aqua gel, lotion, solution, cream, ointment, powder puff, dressing, foam, film, patch, wafer, implant, sponge, fiber, bandage, micro emulsion, as well as liposome. The typical carriers include alcohol, water, mineral oil, liquid paraffin, white petrolatum, glycerol, polyethylene glycol and propylene glycol. Penetration enhancers can also be added in, as referred, for example, in J Pharm Sci, 88 (10), 955-958, Finnin and Morgan (October 1999).

Formulations suitable for topical application in the eye are, for example, eye drops, in which the invented compounds are dissolved or suspended in appropriate carriers. The typical formulations for topical uses in the eye or the ear can be drops of micronized suspension, or drops of solution prepared in sterile, isoentropic and pH-adjusted saline. Other formulations suitable for topical application in the eye and in the ear include ointments, biodegradable (e.g., absorbable gel sponges, collagens) or non-biodegradable (e.g., silicones), wafers, lenses, and micro particle or vesicular systems, such as niosomes or liposomes. Polymers, such as cross-linked polyacrylic acid, polyvinyl alcohol, hyaluronic acid, cellulose polymers (e.g., hydroxypropyl methyl cellulose, hydroxyethyl cellulose or methyl cellulose) or heteropolysaccharide polymers (e.g., agarose gel), can be mixed with preservatives (e.g., benzalkonium chloride). These formulations can be delivered by iontophoresis.

For intranasal application or inhalation, the invented active compounds are formulated as solution or suspension that can be conveniently delivered via manual or electrical spray pump; as dry powder (alone, blended with such as lactose, or mixed with phospholipid such as lecithin to form dry particles) that can be delivered via dry powder inhaler; or as spray that can be delivered via pressurized container, pump, nebulizer, atomizer (preferably electrohydraulic atomizer generating fine sprays) or sprayer with or without propellant such as 1, 1, 1, 2-tetrafluoroethane or 1, 1, 1, 2,3, 3, 3-heptafluoropropane. The powder for intranasal application can contain bioadehesives, such as chitosan or cyclodextrin.

In another preferred embodiment, the invented active compounds are formulated for rectal administration, such as rectal suppository. Suppository matrix can be commonly used cocoa butter or various other equivalents.

Other carrier materials and administration methods known in the pharmaceutical industry can also be used. Pharmaceutical compositions described in the present invention can be formulated by any method known in pharmaceutics, such as efficient preparation and application procedures, which are well known in the field and described in standard textbooks, such as in Hoover, John E., Remington's Pharmaceutical Sciences. Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients (3rd Ed.), American Pharmaceutical Association, Washington, 1999.

Combined Use

The compounds described in the present invention can be used alone or combined with other therapeutics simultaneously (same formulation or individual formulations) or sequentially, in order to treat multiple diseases or disease conditions.

Combined use of two or more compounds refers to when the time intervals between the administrations of two or more compounds are sufficiently short, so that the presence of one compound affects the biological effects of the other compound(s). The co-administration can be simultaneous, coexisting, or sequential. In addition, the conjunctive use can be carried out with premixed compounds, or at a same time point but via a different anatomical position or a different route.

The terms "combined use", "co-administration" or "conjunctive use" refer to combined use of the compounds.

FIGURE LEGENDS

FIG. 1. The docking results of the ATP-binding domain of CDK2 and the compound 75 or 7-azaindirubin.

The dotted line in green represents the hydrogen bonding interaction. Oxygen (0) is labeled as red; nitrogen (N), as blue; hydrogen (H), as white; and carbon (C), as grey. (a) The H at position N1 and the O at position 2 in both compounds form hydrogen bonding with their respective amino acid residues in the ATP binding pocket of CDK2. The docking score is 99.294 for the compound 75 (right); 102.251, for 7-azaindirubin (left). (b) Similarity of interactions between the ATP-binding pocket with the compound 75, and with 7-azaindirubin. The docking software used was Discovery Studio. The docking method was LibDock. The three dimensional structure of CDK2 was from CDK2/cyclinA co-crystallized with sulfonyl-indirubin.

Figure 2:
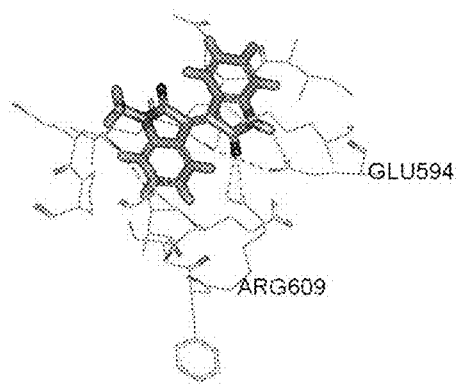
Figure 2:
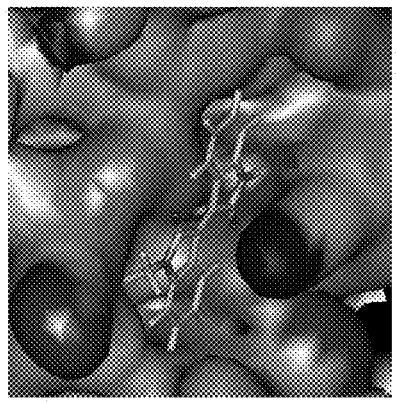
Figure 2:
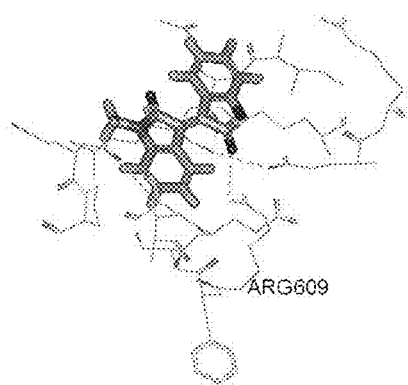
Figure 2:
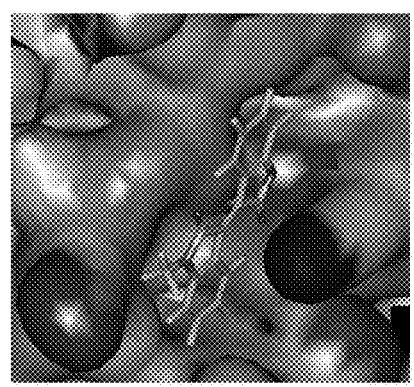
Figure 2:
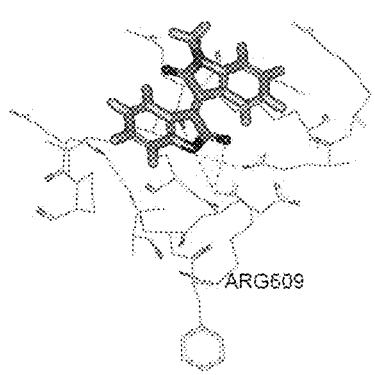
Figure 2:
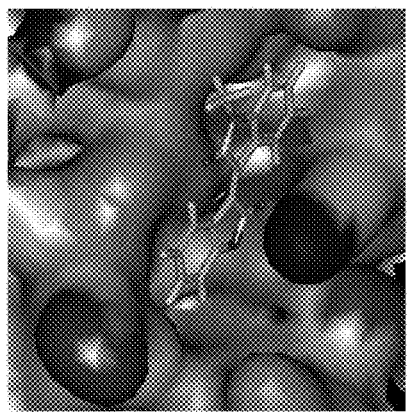

FIG. 2. The docking results of the SH2 domain of STAT3 and the compound-93 or N-methyl-isoindigo.

The dotted lines in green in the left of the figure represent the hydrogen bonding interaction. Oxygen (O) is labeled as red; nitrogen (N), as blue; hydrogen (H), as white; and carbon (C), as yellow. (d1): the H at position N-1' and the O at position 2' of N-methyl-isoindigo form hydrogen bonds with respective residues of amino acids in the binding pocket in the SH2 domain of the human STAT3 protein. LibDockScore: 93.9797; (d2, d3)): the O at position 1' and the O at position 2' of N-methyl-1'-oxo-isoindigo form hydrogen bonds with respective residues of amino acids in the binding pocket in the SH2 domain of human STAT3 protein. LibDockScore is 91.0665 for N-methyl-1'-oxo-isoindigo positioned at the same binding format as N-methyl-isoindigo (d2); LibDockScore is 94.5181 for N-methyl-1'-oxo-isoindigo positioned at the 180 degree-reversed structural plane as that of N-methyl-isoindigo (d3), a higher score suggesting a more favorable docking position. The dockings shown in the right of the figures (d1~d3) indicate a clear similarity between the interactions of STAT3-SH2 with N-methyl-isoindigo, and with N-methyl-1'-oxo-isoindigo. The three dimensional structure of STAT3-SH2 domain was from a crystallized form of STAT3 with AAPpYL. The docking software was Discovery Studio. The docking method was LibDock.

DETAILED PREPARATION METHODS

The present invention is further demonstrated as followings, with individual examples together with the figures. It should be understood that the described examples are used only to illustrate the present invention, not to limit the scope of the present invention.

I. Method for Chemical Syntheses

I-1. Syntheses of Intermediates and Target Compounds of 1-oxo-indirubins (I-1~3)

I-1-1. Syntheses of the Intermediates N1-substituted Indole-2,3-dione (A1) and N1-substituted-5/7-azaindole-2,3-dione (A2/A3)

N1-alkyl-indole-2,3-dione (A1) was synthesized by alkylating the N-1 position of isatins that have desired substituents at different positions;

N1-alkyl-5-azaindole-2,3-dione (A2) and N1-alkyl-7-azaindole-2,3-dione (A3) were synthesized by alkylating the N-1 position of 5-azaindole and 7-azaindole, respectively, that have desired substituents at different positions, then oxidizing the intermediates in the presence of $CrO_3$ and $CH_3COOH$.

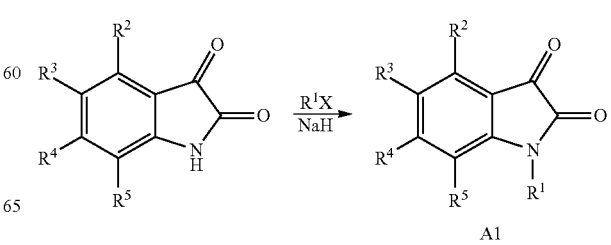

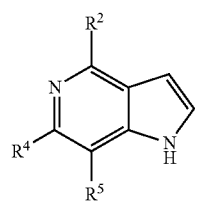

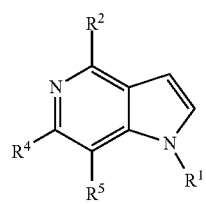

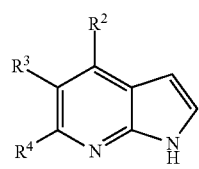

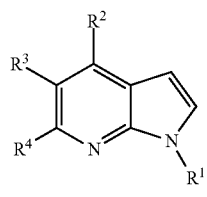

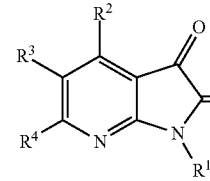

Wherein, $R^1$ represents $CH_3$, $C_2H_5$, n-$C_3H_7$, n-$C_4H_9$, $PhCH_2$, glycosyl protected by acyl, etc.; $R^2$, $R^3$, $R^4$, $R^5$ independently represent H, D, halogen, hydroxyl, sulfhydryl, $C_1$~$C_4$ alkyl, nitro, amino, amido, amide, $C_1$~$C_4$ alkoxy, methylthio, phenyl, phenoxy, aryl, aralkyl, trifluoromethyl, acyl, aroyl, sulfonyl, isocyanate;

I-1-2. Syntheses of the Intermediates, Benzofurane-3-one (B)

Benzofurane-3-ones (B) were synthesized by esterification of salicylic acid that has desired substituents at different positions, substitution reaction with ethyl chloroacetate, hydrolytic reaction of the esters, cyclization of anhydride acid, and then hydrolytic reaction under acidic condition.

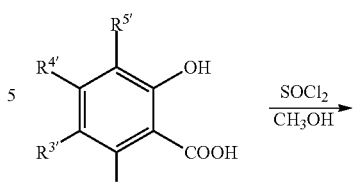

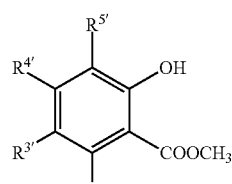

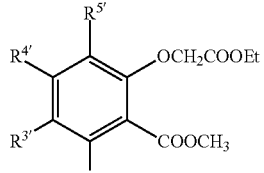

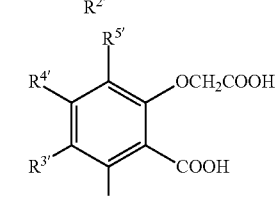

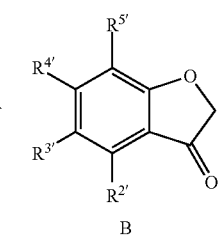

Wherein, $R^{2'}$, $R^{3'}$, $R^{4'}$ and $R^{5'}$ independently represent H, D, halogen, hydroxyl, sulfhydryl, $C_1$~$C_4$ alkyl, nitro, amino, amido, amide, $C_1$~$C_4$ alkoxy, methylthio, phenyl, phenoxy, aryl, aralkyl, trifluoromethyl, acyl, aroyl, sulfonyl, isocyanate.

I-1-3. Syntheses of 1-oxo-(aza)indirubins (I-1~3)

The target compounds were synthesized through reactions of benzofurane-3-ones (B) and N1-alkyl-indole-2,3-diones (A1) or N1-alkyl-5-azaindole-2,3-diones (A2) or N1-alkyl-7-azaindole-2,3-diones (A3) using acetic acid as solvent in the presence of sodium acetate anhydrous under condition of 85° C. for 8 hours with stirring. The reactions were terminated by pouring the reaction mixture into ice water in which the products crystallized into solids. The target products (I-1, I-2, and I-3) were obtained by filtration, desiccation, and purification through column chromatography.

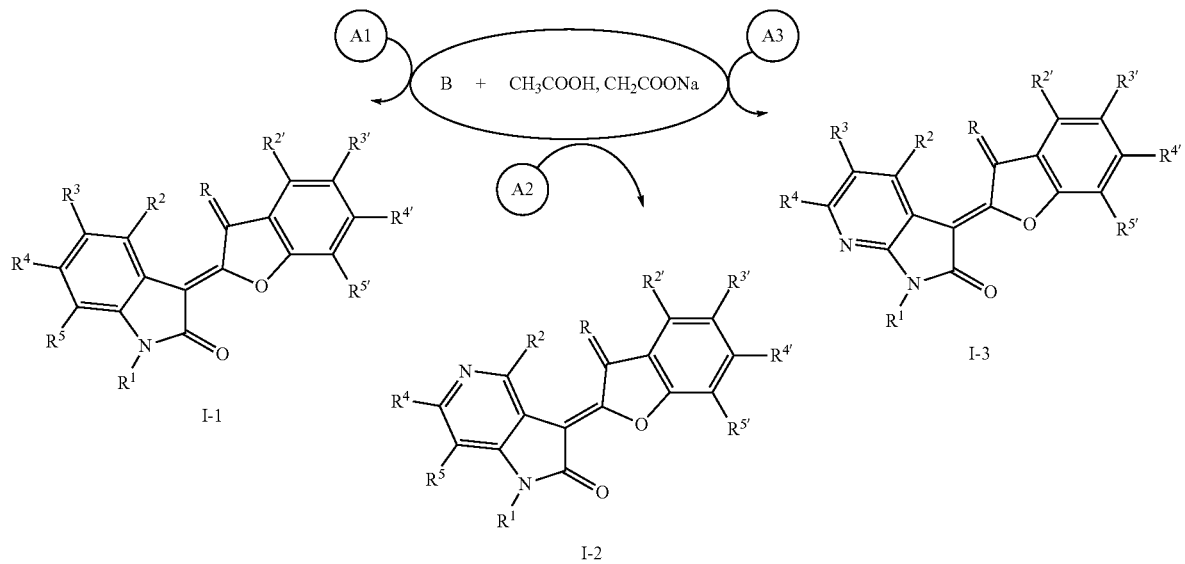

Wherein, $R^1$ represents H or D, $C_1$~$C_6$ alkyl, aryl, aralkyl, acyl, aroyl, glycosyl or biosyl protected by acyl, glycosyl or biosyl; $R^2$, $R^3$, $R^4$, $R^5$, $R^{2'}$, $R^{3'}$, $R^{4'}$ and $R^{5'}$ independently represent H, halogen, hydroxyl, sulfhydryl, $C_1$~$C_4$ alkyl, nitro, amino, amido, amide, $C_1$~$C_4$ alkoxy, methylthio, phenyl, phenoxy, aryl, aralkyl, trifluoromethyl, acyl, aroyl, sulfonyl, sulfamoyl, isocyanate, or alkyl isocyanate;

Wherein R represents oxygen, sulfur, selenium, or a $NR^6$ or $NOR^6$ group, wherein $R^6$ is H, $C_1$~$C_6$ straight-chain or branched-chain alkyl, aryl, aralkyl, $C_3$~$C_6$ alicyclic group, acyl, aroyl, sulfonyl or phosphoryl.

I-1-4. Syntheses of the Target Compounds, 3'-oxime-1'-oxo-indirubins

3'-oxime-1'-oxo-indirubins were synthesized through heating reflux of hydroxylamine hydrochloride with N1-alkyl-(aza)indirubins in pyridine.

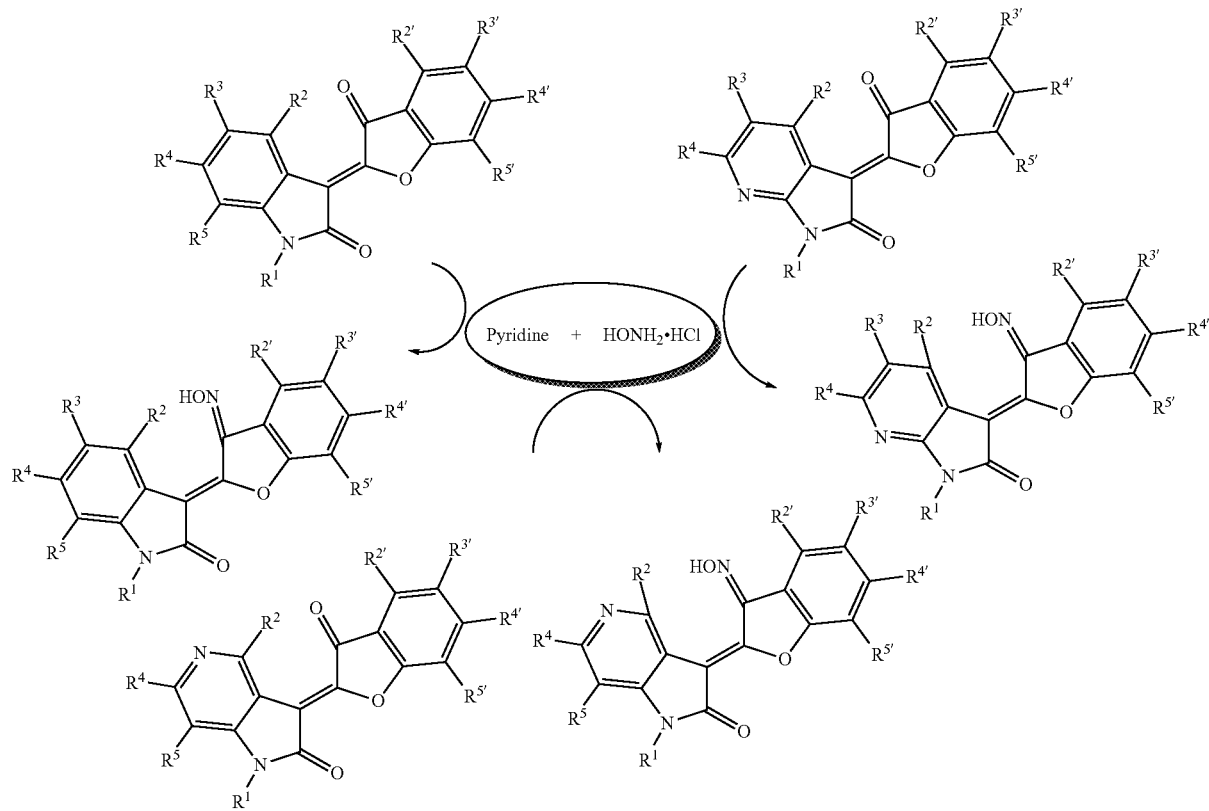

Wherein $R^1$, $R^2$, $R^3$, $R^4$, $R^5$, $R^{2'}$, $R^{3'}$, $R^{4'}$ and $R^5$ represent the same as described in "1-3".

I-1-5. Syntheses of Target Compounds, 1'-oxo-indirubins-3'-oxime Ester

1'-oxo-indirubins-3'-oxime ester were synthesized by reacting 3'-oxime-1'-oxo-indirubins with halocarbon in alkaline alcohol solution.

I-2. Syntheses of Intermediates and Target Compounds of 1-oxo-isoindigos (II-1~3)

Syntheses of the key intermediates: Benzofuran-2-ones (C) are actually the lactones of salicylic acid derivatives. They are commercially available. The target compounds were synthesized through reactions of benzofurane-2-ones (C) and N1-alkyl-indole-2,3-diones (A1) or N1-alkyl-5-azaindole-2,3-diones (A2) or N1-alkyl-7-azaindole-2,3-di-

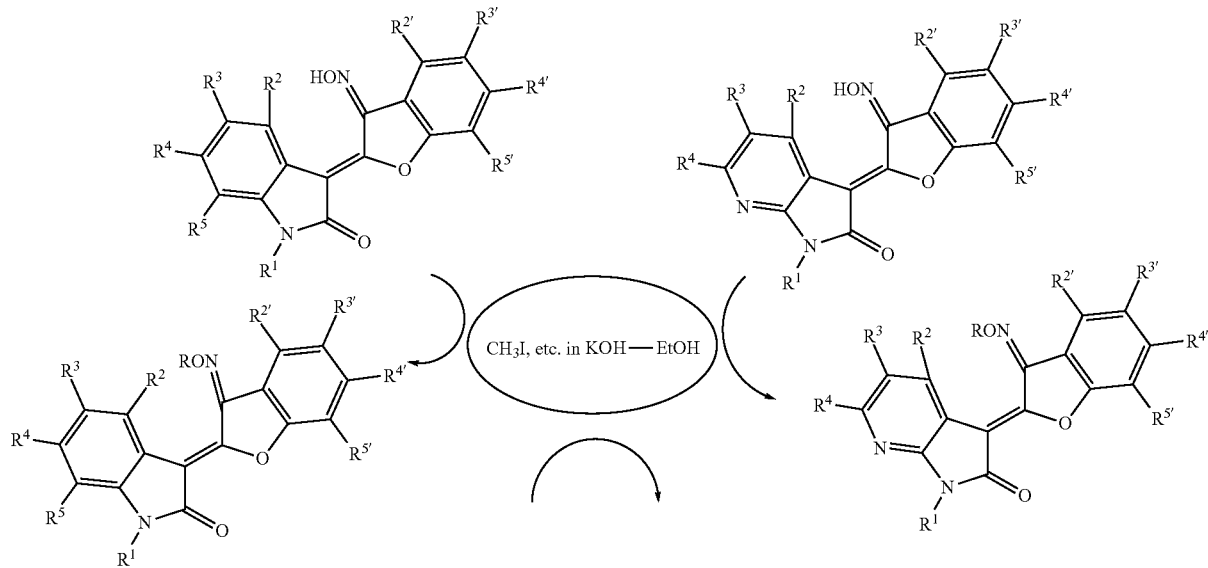

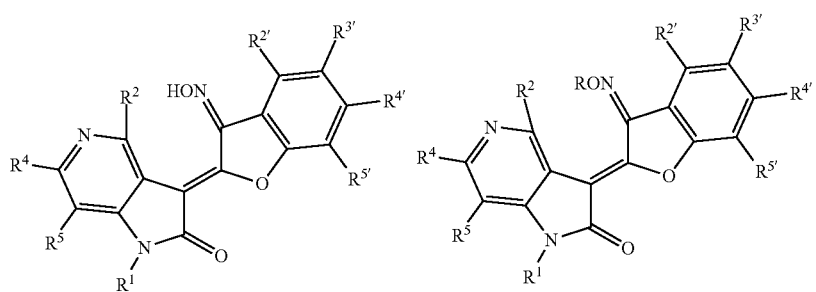

Wherein R represents $CH_3ON$, EtON; $R^1$ represents $CH_3$, $C_2H_5$, n-$C_3H_7$, n-$C_4H_9$, $PhCH_2$, etc.; $R^{2'}$, $R^{4'}$ represent H, $CH_3$, $C_2H$, n-$C_3H_7$, n-$C_4H_9$, $PhCH_2$, etc.

ones (A3) using acetic acid as solvent in the presence of sodium acetate anhydrous under condition of 85° C. for 8 hours with stirring. The reactions were terminated by pouring the reaction mixture into ice water in which the products became crystallizing solid. The target products (II-1, II-2, and II-3) were obtained by filtration, desiccation, and purification through column chromatography.

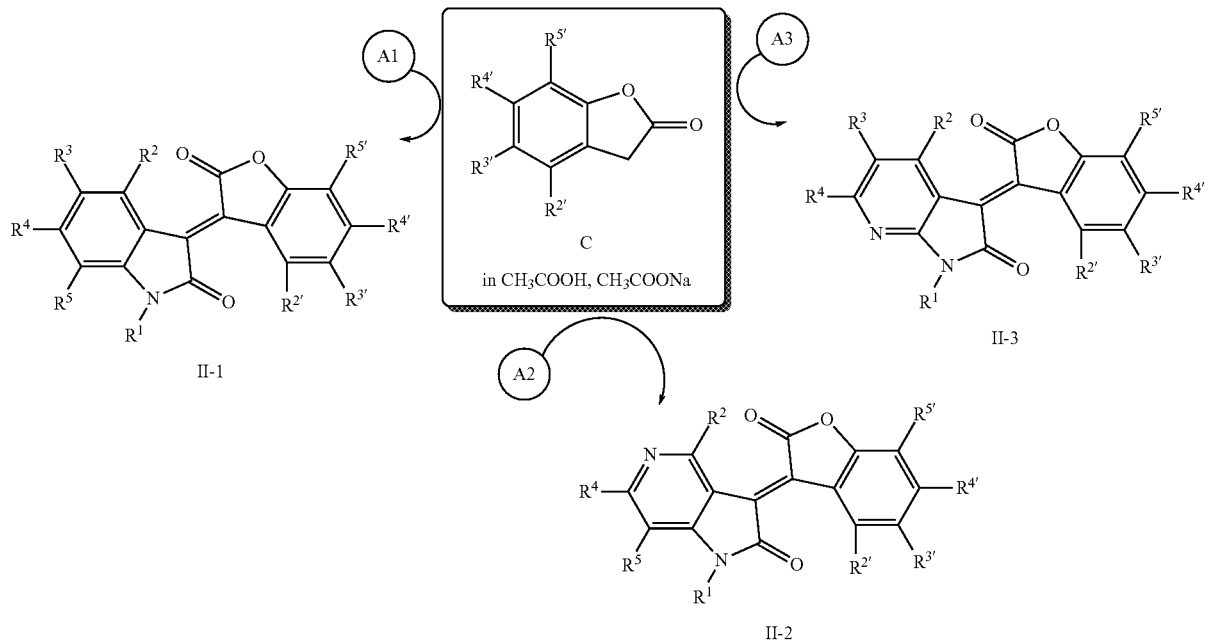

Wherein, $R^1$ represents H or D, $C_1$~$C_6$ alkyl, aryl, aralkyl, acyl, aroyl, glycosyl or biosyl protected by acyl, glycosyl or biosyl; $R^2$, $R^3$, $R^4$, $R^5$, $R^{2'}$, $R^{3'}$, $R^{4'}$ and $R^{5'}$ independently represent H, halogen, hydroxyl, sulfhydryl, $C_1$~$C_4$ alkyl, nitro, amino, amido, amide, $C_1$~$C_4$ alkoxy, methylthio, phenyl, phenoxy, aryl, aralkyl, trifluoromethyl, acyl, aroyl, sulfonyl, sulfamoyl, isocyanate, or alkyl isocyanate.

II. Exemplification of Chemical Synthesis

The present invention is further illustrated through the following examples. It should be appreciated that the following examples are provided merely for the purposes of illustration and not intended to limit the scope of the invention. In examples, the experimental methods usually follow conventional methods or recommendations from manufacturers, unless specifically indicated. Unless otherwise indicated, the portion and percentage are mass portion and weight percentage.

II-1. Instruments and Reagents

The melting points of 1'-oxo-(aza)indirubins and 1'-oxo-(aza)isoindigos presented in this example were measured by the Mel-TEMP melting point instrument without calibration. Infra-red (IR) spectrum was measured by the Nicolet Avatar 370 DTGS IR spectrometer. The electrospray ionization mass spectrum (ESI-MS) was determined using the HP1100LC/MSD mass spectrometer; the high resolution MS was determined by the Agilent Q-TOF 6520 high resolution mass spectrometer. The thin layer chromatographic (TLC) plates were made from silica gel GF254 (Qingdao Haiyang Chemical Co., Ltd) and 0.8% CMC-Na solution in distilled water, activated at 100-110° C. for 1 hour, preserved in dryers, and developed under ultraviolet light (at 254 nm and 365 nm). The chromatographic columns were packed by the dry method with silica gel (100-200 mesh or 200-300 mesh) (Qingdao Haiyang Chemical Co., Ltd). The hydrogen spectrum ($^1$H-NMR) was determined by the Bruck AV-300 nuclear magnetic resonance spectrometer using tetramethylsilane (TMS) as an internal standard. The elemental analysis was performed using the Elementar Vario EL. III elemental analyzer.

The reagents were commercially available chemically pure (CP) or analytical reagents (AR). Unless otherwise indicated, the reagents were used directly without any prior treatment.

II-2. Example: Preparation of the Compounds

II-2-1. Preparation of the Intermediates

Example 1: Preparation of the Intermediate, N1-benzyl-indole-2,3-dione (A1)

To a solution of indole-2,3-dione (1.0 g, or 0.007 mol) in 10 ml DMF (N,N-Dimethylformamide) incubated in ice water, NaH (0.24 g, or 0.01 mol) was slowly added; 10 minutes later, benzyl chloride (0.88 g, 0.007 mol) was added; and the reaction mixture was incubated under room temperature while stirring for 9 hours. The reaction was terminated by pouring the reaction mixture into ice water in which the products became crystallized red solids. TLC showed that the reaction mixture still contained a small amount substrate. The target product was obtained by filtration, desiccation, and purification through column chromatography (petroleum ether: ethyl acetate=4: 1). A solid red product of 0.85 g was obtained, with a yield of 59%; ESI-MS m/z: 238.2 [M+H]$^+$, $C_{15}H_{11}NO_2$ (237.3).

Example 2: Preparation of the Intermediate, N1-methyl-5-azaindole-2,3-dione (A2)

To a solution of 1-methyl-5-azaindole (2.0 g, or 15 mmol) in 70 ml acetic acid, a suspension of 3.2 g $CrO_3$ in 20 ml water was added. The reaction mixture was stirred for 0.5 h at room temperature (the reaction was monitored by TLC), and then diluted with water. The product was extracted using trichloromethane three times; the combined organic phases were washed with water, dried and evaporated. An orange product (1-methyl-5-azaindole-2,3-dione) of 1.5 g was obtained, with a yield of 62%; mp: 140-142° C.

Example 3: Preparation of the Intermediate, N1-methyl-7-azaindole-2,3-dione (A3)

To a solution of N1-methyl-7-azaindole (1.01 g, or 7.65 mmol) in 30 ml acetic acid (AcOH), a suspension of 1.5 g $CrO_3$ in 10 ml water was added. The reaction mixture was stirred for 0.5 h at room temperature (the reaction was kept tracked by TLC), and then diluted with water. The product was extracted using trichloromethane three times; the combined organic phases were washed with water, dried and evaporated. A yellow solid product (1-methyl-5-azaindole-2,3-dione) of 1.0 g was obtained, with a yield of 84%; mp: 159-160° C. (mp reported in literature: 160-161° C.) (Tatsugi, et al., An improved preparation of isatins from indoles. ARKIVOC 2001; (i) 67-73).

Example 4: Preparation of the Intermediate, benzofuran-3-one (B)

(1) Methyl Salicylate

To a solution of salicylate (30 g, or 0.217 mol) in 150 ml absolute methanol in a 500 ml-three-necked bottle, 90 ml thionyl chloride was slowly added with a dropping funnel. A lot of heat was released during this procedure. The reaction mixture was then heated and refluxed for 5 hours, during which the reaction was monitored by TLC. The mixture was cooled down and then poured into a 250 ml eggplant-shaped bottle, and 200 ml ethyl acetate was added after the methanol was removed by rotary evaporation under reduced pressure. The reaction mixture was washed 3 or more times until the fluorescence disappeared from the water and the ethyl acetate phase became pH-neutral. The product was desiccated with anhydrous sodium sulfate, filtered to remove the desiccant, and dried by decompression evaporation. A colorless liquid of 32.15 g, a yield of 98%, was obtained after purification through column chromatography (petroleum ether: ethyl acetate=5:1) and was ready for the next reaction.

(2) 2-Ethoxycarbonyl Methoxyl-Methyl Benzoate

The methyl salicylate (32.15 g, or 0.213 mol) obtained from previous reaction was dissolved and mixed well in 150 ml acetone, added with $K_2CO_3$ (72 g, or 0.727 mol) and ethyl chloroacetate (22.5 ml, or 0.211 mol). The mixture was heated and refluxed for 11 hours, after which the reaction was terminated and the acetone was removed by rotary evaporation under reduced pressure. The reaction mixture was dissolved in water, extracted multiple times with ethyl acetate, desiccated with anhydrous sodium sulfate, filtered to remove the desiccant, and then dried by decompression evaporation. A milk-white solid of 48 g, a yield of 94%, was obtained after purification through column chromatography (petroleum ether: ethyl acetate=5: 1) and was ready for the next reaction.

(3) 2-Carboxymethyloxy Benzoic Acid

The 2-ethoxycarbonyl methoxyl-methyl benzoate (48 g, or 0.201 mol) obtained from the previous reaction was dissolved in 60 ml methanol and added with 300 ml of 10% $K_2CO_3$ solution. The mixture was stirred at room temperature for 3 hours; the reaction was then terminated and the methanol was removed by rotary evaporation under reduced pressure. The reaction mixture was added with concentrated HCl and stirred until a white solid separated out with an acidic pH. The product was filtered, washed with water and desiccated under infrared lamp. A white solid of 18.15 g, a yield of 46%, was obtained and was ready for the next reaction.

(4) 3-Acetoxyl-Benzofuran

The 2-carboxymethyloxy benzoic acid (18.15 g) obtained from previous reaction was divided into 2 parts, 9 g and 9.15 g for two separate reactions. The 2-carboxymethyloxy benzoic acid (9 g, or 0.046 mol) together with the anhydrous sodium acetate (11.88 g) were dissolved in 300 ml acetic anhydride and 47.25 ml acetic acid, stirred and heat-refluxed for 4 hours. The reaction mixture was cooled down and added with 400 ml water, thoroughly mixed, and extracted with dichloromethane. The dichloromethane phase was repeatedly washed with saturated sodium bicarbonate solution, and then with saturated sodium chloride solution. For the remaining 2-carboxymethyloxy benzoic acid (9.15 g, or 0.047 mol), the same molar ratios of raw materials and procedures as described above were used in the same reactions. A combined product of 11.06 g, a final yield of 68%, was obtained, and was ready for the next reaction.

(5) Benzofuran-3-One

The 3-acetoxyl-benzofuran (11.06 g, or 0.058 mol) obtained from the previous reaction was dissolved in 80 ml methanol, added with 2.5 ml concentrated HCl, and then with 25 ml water, stirred, heat-refluxed for 1 hour. The reaction mixture was then cooled down in ice water. The light-yellow product was crystallized, filtered, desiccated under infrared lamp. The final product obtained was 6.63 g, with a yield of 79%; ESI-MS m/z: 135.1[M+H]$^+$, $C_8H_6O_2$ (134.1).

II-2-2. Preparation of the Representative Target Compounds (I-1~3)

Example 5: N1-benzyl-1'-oxo-indirubin (14)

N1-benzyl-indole-2,3-dione (0.35 g, or 1.5 mmol) was dissolved in 15 ml acetic acid, added with anhydrous sodium acetate (0.37 g, or 4.5 mmol) solid, stirred until dissolved and then added with benzofuran-3-one (0.2 g, or 1.5 mmol). The reaction was maintained at 85° C. for 8 hours and then terminated. The cooled reaction mixture was poured into 200 ml ice water and thoroughly mixed. A maroon solid was crystallized, filtered, desiccated, and purified through column chromatography (dichloromethane: ethyl acetate=120: 1, then, petroleum ether: ethyl acetate=6:1, v/v). The product was re-crystallized with dichloromethane and petroleum ether. 0.26 g of the purified red solid product was obtained, with a yield of 48%, m.p. 235~237° C.; IR (KBr, v, cm$^{-1}$): 3435, 3326, 3318, 1706, 1654, 1595, 1465, 1400, 1361, 1305, 1162, 1081, 954;

ESI-MS m/z: 392.2[M+K]$^+$, $C_{23}H_{15}NO_3$(353.4);

$^1$H-NMR (DMSO-d6, 300 MHz) δ: 8.92 (d, J=7.60 Hz, 1H, Ar—H), 7.86 (t, J=7.00 Hz, 2H, Ar—H), 7.56 (d, J=7.80 Hz, 1H, Ar—H), 7.35~7.32 (m, 7H, Ar—Hs), 7.10 (t, J=7.60 Hz, 1H, Ar—H), 6.71 (d, J=7.80 Hz, 1H, Ar—H), 4.99 (s, 2H, Ar—CH2);

Anal. for $C_{23}H_{15}NO_3$ Calcd (%): C, 78.17; H, 4.28; N, 3.96.

Found (%): C, 78.09; H, 4.40; N, 3.68.

Example 6: N1-Benzyl-1'-Oxo-Indirubin-3'-Oxime (38)

N1-benzyl-1'-oxo-indirubin (0.2 g, or 0.57 mmol) was dissolved in 12 ml methanol, added with 4 ml anhydrous pyridine and 0.1 g (1.4 mmol) hydroxylamine hydrochloride and heat-refluxed for 1 hour. The reaction mixture was cooled down and concentrated by removing most of the solvent. The remaining mixture was poured into 60 ml ice water and stirred vigorously. An orange solid was crystallized, filtered and purified through silica gel column chromatography (petroleum ether: ethyl acetate=3:1, v/v). 0.16 g orange solid product, N1-benzyl-1'-oxo-indirubin-3'-oxime (38), was obtained, with a yield of 75%; m.p.: 253-255° C.; IR (KBr, v, cm$^{-1}$): 3240, 3060, 3028, 2804, 2775, 1668, 1614, 1589, 1463, 1332, 1213, 1170, 1018, 997, 696;

ESI-MS: 369.1[M+H]$^+$, C$_{23}$H$_{16}$N$_2$O$_3$(368.4);

$^1$H NMR (AV-300, D6-DMSO, ppm) δ: 13.7 (s, 1H, N—OH), 8.90 (d, J=7.60 Hz, 1H, Ar—H), 7.82 (t, J=7.00 Hz, 2H, Ar—H), 7.53 (d, J=8.55 Hz, 1H, Ar—H), 7.32-7.30 (m, 7H, Ar—Hs), 7.11 (t, J=7.60 Hz, 1H, Ar—H), 6.67 (d, J=7.80 Hz, 1H, Ar—H), 4.94 (s, 2H, Ar—CH$_2$);

Anal. for C$_{23}$H$_{16}$N$_2$O$_3$ Calcd (%): C, 74.99; H, 4.38; N, 7.60.

Found (%): C, 74.51; H, 4.60; N, 7.42.

Example 7: N1-benzyl-1'-oxo-indirubin-3'-oxime ether (56)

N1-benzyl-1'-oxo-indirubin-3'-oxime (1.5 g, or 4.1 mmol) was added to 50 ml anhydrous ethanol containing 5% KOH, dissolved in mild heating condition, filtered, added drop wise with 3 ml CH$_3$I while being stirred. Heat was released at this step and dark red precipitate was formed. After stirring for 0.5 hours, the reaction mixture was filtered, water-washed until pH became neutral, and then desiccated. The dark red crude was re-crystallized in acetone. 1.22 g dark red crystal, N1-benzyl-1'-oxo-indirubin-3'-oxime ether (56), was obtained, with a yield of 78%; mp: 201-200° C.;

ESI-MS: 383.0 [M+H]$^+$, C$_{24}$H$_{18}$N$_2$O$_3$(382.4);

$^1$H-NMR (AV-300, D6-DMSO, ppm) δ: 4.26 (s, 3H, O—CH$_3$), 4.88 (s, 2H, N—CH$_2$), 8.92 (d, J=7.60 Hz, 1H, Ar—H), 7.76 (t, J=7.00 Hz, 2H, Ar—H), 7.52 (d, J=8.55 Hz, 1H, Ar—H), 7.30-7.27 (m, 7H, Ar—Hs), 7.11 (t, J=7.60 Hz, 1H, Ar—H), 6.69 (d, J=7.80 Hz, 1H, Ar—H);

Anal For C$_{24}$H$_{18}$N$_2$O$_3$ Calcd (%): C, 75.38; H, 4.74; N, 7.33.

Found (%): C, 75.19; H, 4.59; N, 7.48.

II-2-3. Preparation of all Other Target Compounds (I-1~3)

II-2-3-1. Syntheses of 1'-oxo-indirubin Derivatives (Formula I-1, No. 1~No. 60)

Example 8: Twenty-Four Derivatives of 1'-oxo-indirubin (No. 1~No. 24) were Synthesized by the Method Described Above for the Synthesis of N1-benzyl-1'-oxo-indirubin (14) in Example 5

Example 9: Twenty-Four Derivatives of 1'-oxo-indirubin-3'-oxime (No. 25~No. 48) were Synthesized by the Method Described Above for the Synthesis of N1-benzyl-1'-oxo-indirubin-3'-oxime (38) in Example 6

Example 10: Twelve Derivatives of 1'-oxo-indirubin-3'-oxime ether (No. 49~No. 60) were Synthesized by the Method Described Above for the Synthesis of N1-benzyl-1'-oxo-indirubin-3'-oxime ether (56) in Example 7

Molecular structures of the compounds 1~60 are listed in Table 1. All these novel compounds were structurally characterized by IR, ESI-MS, $^1$H-NMR and elemental analysis.

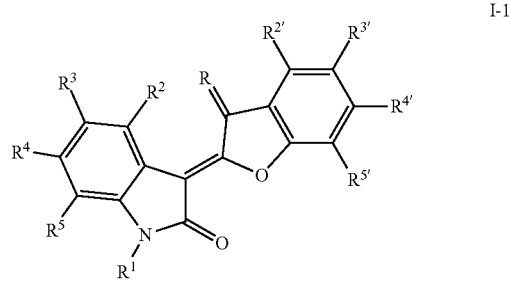

I-1

In the formula I-1, R$^2$, R$^{2'}$, R$^{4'}$ and R$^{5'}$ represent H. Rest of the substituents are described in Table 1:

TABLE 1

Structures of 1'-oxo-indirubins (I-1: 1~60)

| ID | R$^1$ | R$^3$ | R$^4$ | R$^5$ | R$^{3'}$ | R |
|---|---|---|---|---|---|---|
| 1 | H | H | H | H | H | O |
| 2 | H | H | H | F | H | O |
| 3 | CH$_2$CH$_3$ | H | H | H | H | O |
| 4 | CH$_2$CH$_3$ | H | H | F | H | O |
| 5 | CH$_2$CH$_3$ | Cl | H | H | H | O |
| 6 | CH$_2$CH$_3$ | H | Cl | H | H | O |
| 7 | CH$_2$CH$_3$ | CH$_3$ | H | H | H | O |
| 8 | i-C$_3$H$_7$ | H | H | H | H | O |
| 9 | i-C$_3$H$_7$ | F | H | H | H | O |
| 10 | i-C$_3$H$_7$ | H | H | F | H | O |
| 11 | i-C$_3$H$_7$ | Cl | H | H | H | O |
| 12 | i-C$_3$H$_7$ | H | Cl | H | H | O |
| 13 | i-C$_3$H$_7$ | Me | H | H | H | O |
| 14 | CH$_2$Ph | H | H | H | H | O |
| 15 | CH$_2$Ph | F | H | H | H | O |
| 16 | CH$_2$Ph | Cl | H | H | H | O |
| 17 | CH$_2$Ph | Me | H | H | H | O |
| 18 | CH$_2$Ph | F | H | H | H | O |
| 19 | CH$_2$CH$_3$ | H | H | H | Cl | O |
| 20 | CH$_2$CH$_3$ | H | H | F | Cl | O |
| 21 | CH$_2$CH$_3$ | Cl | H | H | Cl | O |
| 22 | CH$_2$CH$_3$ | H | Cl | H | Cl | O |
| 23 | i-C$_3$H$_7$ | Cl | H | H | Cl | O |
| 24 | i-C$_3$H$_7$ | H | Cl | H | Cl | O |
| 25 | H | H | H | H | H | N—OH |
| 26 | H | H | H | F | H | N—OH |
| 27 | CH$_2$CH$_3$ | H | H | H | H | N—OH |
| 28 | CH$_2$CH$_3$ | H | H | F | H | N—OH |
| 29 | CH$_2$CH$_3$ | Cl | H | H | H | N—OH |
| 30 | CH$_2$CH$_3$ | H | Cl | H | H | N—OH |
| 31 | CH$_2$CH$_3$ | CH$_3$ | H | H | H | N—OH |
| 32 | i-C$_3$H$_7$ | H | H | H | H | N—OH |
| 33 | Ribosyl | H | H | H | H | N—OH |
| 34 | i-C$_3$H$_7$ | H | H | F | H | N—OH |
| 35 | i-C$_3$H$_7$ | Cl | H | H | H | N—OH |
| 36 | i-C$_3$H$_7$ | H | Cl | H | H | N—OH |
| 37 | i-C$_3$H$_7$ | Me | H | H | H | N—OH |
| 38 | CH$_2$Ph | H | H | H | H | N—OH |
| 39 | CH$_2$Ph | F | H | H | H | N—OH |
| 40 | CH$_2$Ph | Cl | H | H | H | N—OH |
| 41 | CH$_2$Ph | Me | H | H | H | N—OH |
| 42 | CH$_2$CH$_3$ | F | H | H | H | N—OH |
| 43 | CH$_2$CH$_3$ | H | H | H | Cl | N—OH |
| 44 | CH$_2$CH$_3$ | H | H | F | Cl | N—OH |
| 45 | CH$_2$CH$_3$ | Cl | H | H | Cl | N—OH |
| 46 | CH$_2$CH$_3$ | H | Cl | H | Cl | N—OH |
| 47 | i-C$_3$H$_7$ | Cl | H | H | H | N—OH |
| 48 | i-C$_3$H$_7$ | H | Cl | H | Cl | N—OH |
| 49 | H | H | H | H | H | N—OCH$_3$ |
| 50 | H | H | H | F | H | N—OCH$_3$ |
| 51 | CH$_2$CH$_3$ | H | H | H | H | N—OCH$_3$ |
| 52 | CH$_2$CH$_3$ | H | H | F | H | N—OCH$_3$ |
| 53 | Glucosyl | Cl | H | H | H | N—OCH$_3$ |
| 54 | i-C$_3$H$_7$ | H | Cl | H | H | N—OCH$_3$ |
| 55 | i-C$_3$H$_7$ | Me | H | H | H | N—OCH$_3$ |
| 56 | CH$_2$Ph | H | H | H | H | N—OCH$_3$ |

TABLE 1-continued

Structures of 1'-oxo-indirubins (I-1: 1~60)

| ID | $R^1$ | $R^3$ | $R^4$ | $R^5$ | $R^{3'}$ | R |
|---|---|---|---|---|---|---|
| 57 | $CH_2Ph$ | F | H | H | H | N—$OCH_3$ |
| 58 | $CH_2Ph$ | Cl | H | H | H | N—$OCH_3$ |
| 59 | $CH_2CH_3$ | F | H | H | H | N—$OCH_3$ |
| 60 | i-$C_3H_7$ | H | Cl | H | Cl | N—$OCH_3$ |

II-2-3-2. Syntheses of 1'-oxo-5-azaindirubin Derivatives (Formula I-2, No. 61~No. 74)

Example 11: Synthesis of N-butyl-1'-oxo-5-azaindirubin (69)

N1-butyl-5-azaindole-2,3-dione (0.31 g, or 1.5 mmol) was dissolved in 15 ml acetic acid, added with 0.37 g anhydrous sodium acetate (4.5 mmol) solid, stirred until dissolved and then added with 0.2 g benzofuran-3-one (1.5 mmol). The reaction was maintained at 85° C. for 8 hours and then terminated. The cooled reaction mixture was poured into 200 ml ice water and thoroughly mixed. A maroon solid was crystallized, filtered, desiccated, and purified through column chromatography (dichloromethane: ethyl acetate=5: 1, v/v). The crude product was re-crystallized with dichloromethane and petroleum ether. 0.26 g of the purified maroon solid product, N-butyl-1'-oxo-5-azaindirubin (69), was obtained, with a yield of 52%, m.p. 141~143° C.; IR (KBr, v, cm$^{-1}$): 3428, 3290, 3133, 2946, 1675, 1627, 1612, 1594, 1455, 1402, 1384, 1197, 1116, 981, 748; $^1$H-NMR(CDCl$_3$, 300 MHz) δ: 8.91 (dd, J=0.90, 7.80 Hz, 1H, Ar—H), 8.43 (d, J=7.60 Hz, 1H, Ar—H), 8.02 (dd, J=0.90, 7.80 Hz, 1H, Ar—H), 7.33 (t, J=7.72 Hz, 1H, Ar—H), 7.10 (t, J=7.72 Hz, 1H, Ar—H), 6.98 (m, 1H, Ar—H), 6.86 (d, J=7.60 Hz, 1H, Ar—H), 167-176 (m, 4H, N—CH$_2$CH$_2$—), 1.41-1.45 (m, 2H, CH$_2$), 0.99 (s, 3H, CH$_3$);

ESI-MS m/z: 359.2[M+K]$^+$, $C_{19}H_{16}N_2O_3$(320.3);

Anal. for $C_{19}H_{16}N_2O_3$ Calcd (%): C, 71.24; H, 5.03; N, 8.78.

Found (%): C, 71.05; H, 5.10; N, 8.69.

Example 12: Fourteen Derivatives of 1'-oxo-5-azaindirubin (Formula I-2, No. 61~No. 74) were Synthesized by the Methods Described Above for the Syntheses of N-butyl-1'-oxo-5-azaindirubin (69) in Example 11, 1'-oxo-indirubin-3'-oxime (38) in Example 6, and 1'-oxo-indirubin-3'-oxime ether (56) in Example 7

Molecular structures of the compounds 61-74 are listed in Table 2. All these novel compounds were structurally characterized by IR, ESI-MS, $^1$H-NMR and elemental analysis.

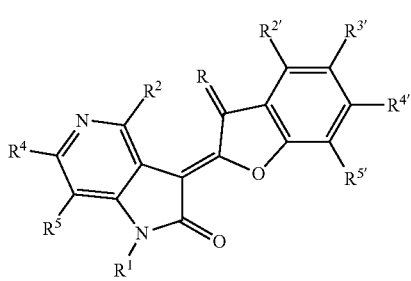

I-2

In the formula I-2, R2', $R^{4'}$ and $R^{5'}$ represent H. Rest of the substituents are described in Table 2.

TABLE 2

Structures of 1'-oxo-5-azaindirubins (I-2: 61-74)

| ID | $R^1$ | $R^2$ | $R^4$ | $R^5$ | $R^{3'}$ | R |
|---|---|---|---|---|---|---|
| 61 | H | H | H | H | H | O |
| 62 | $CH_3$ | H | H | H | H | O |
| 63 | $CH_2CH_3$ | H | H | H | H | O |
| 64 | $CH_2CH_3$ | H | H | F | H | O |
| 65 | $CH_2CH_3$ | $CH_3$ | H | H | H | O |
| 66 | i-$C_3H_7$ | H | H | H | H | O |
| 67 | i-$C_3H_7$ | H | H | F | H | O |
| 68 | i-$C_3H_7$ | Me | H | H | H | O |
| 69 | n-$C_4H_9$ | H | H | H | H | O |
| 70 | n-$C_4H_9$ | H | H | F | H | O |
| 71 | $CH_2CH_3$ | H | H | H | Cl | O |
| 72 | $CH_2Ph$ | H | H | H | H | N—OH |
| 73 | $CH_2CH_3$ | H | H | H | Cl | N—OH |
| 74 | $CH_2Ph$ | H | H | H | H | N—$OCH_3$ |

II-2-3-3. Syntheses of 1'-oxo-7-azaindirubin Derivatives (Formula I-3, No. 75~No. 90)

Example 13: Synthesis of N-isopropyl-1'-oxo-7-azaindirubin (80)

N-isopropyl-7-azaindole-2,3-dione (0.29 g, or 1.5 mmol) was dissolved in 15 ml acetic acid, added with 0.37 g anhydrous sodium acetate (4.5 mmol) solid, stirred until dissolved and then added with 0.2 g benzofuran-3-one (1.5 mmol). The reaction was maintained at 85° C. for 8 hours and then terminated. The cooled reaction mixture was poured into 200 ml ice water and thoroughly mixed. A red solid was crystallized, filtered, desiccated and purified through column chromatography (dichloromethane: ethyl acetate=5: 1, v/v). The crude product was re-crystallized with dichloromethane and petroleum ether. 0.20 g of the purified red solid product, N-isopropyl-1'-oxo-7-azaindirubin (80), was obtained, with a yield of 43%, m.p. 215~216° C.; IR (KBr, v, cm$^{-1}$): 3411, 3307, 3101, 2981, 1700, 1658, 1592, 1467, 1429, 1371, 1315, 1253, 1180, 1097, 1054, 781, 744;

$^1$H-NMR (CDCl$_3$, 300 MHz) δ: 8.92 (dd, J=1.15, 7.80 Hz, 1H, Ar—H), 8.44 (d, J=7.80 Hz, 1H, Ar—H), 7.99-8.03 (m, 1H, Ar—H), 7.31-7.35 (m, 1H, Ar—H), 7.10 (d, J=7.80 Hz, 1H, Ar—H), 7.04 (d, J=7.80 Hz, 1H, Ar—H), 6.97 (dd, J=1.15, 7.80 Hz, 1H, Ar—H), 4.70 (m, 1H, N—CH), 1.55 (d, 6H, 2CH$_3$);

ESI-MS m/z: 339.1[M+Na]$^+$, $C_{18}H_{14}N_2O_3$(306.3)

Anal. for $C_{18}H_{14}N_2O_3$ Calcd (%): C, 70.58; H, 4.61; N, 9.15.

Found (%): C, 70.46; H, 4.52; N, 9.04.

Example 14: Sixteen Derivatives of 1'-oxo-7-azaindirubin (Formula I-3, No. 75~No. 90) were Synthesized by the Methods Described Above for the Syntheses of N-isopropyl-1'-oxo-7-azaindirubin (80) in Example 13, 1'-oxo-indirubin-3'-oxime (38) in Example 6, and 1'-oxo-indirubin-3'-oxime ether (56) in Example 7

Molecular structures of the compounds 75-90 are listed in Table 3. All these novel compounds were structurally characterized by IR, ESI-MS, $^1$H-NMR and elemental analysis.

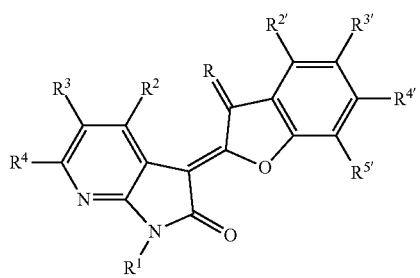

I-3

In the formula I-3, R2, $R^{2'}$ and $R^{4'}$ represent H. Rest of the substituents are described in Table 3.

TABLE 3

Structures of 1'-oxo-7-azaindirubins (I-3: 75-90)

| ID | $R^1$ | $R^3$ | $R^4$ | $R^{3'}$ | $R^{5'}$ | R |
|---|---|---|---|---|---|---|
| 75 | H | H | H | H | H | O |
| 76 | $CH_3$ | H | H | H | H | O |
| 77 | $CH_2CH_3$ | H | H | H | H | O |
| 78 | $CH_2CH_3$ | F | H | H | H | O |
| 79 | $CH_2CH_3$ | H | H | H | Cl | O |
| 80 | $i-C_3H_7$ | H | H | H | H | O |
| 81 | $i-C_3H_7$ | F | H | H | H | O |
| 82 | $i-C_3H_7$ | Cl | H | H | H | O |
| 83 | $i-C_3H_7$ | H | Cl | H | H | O |
| 84 | $i-C_3H_7$ | Me | H | H | H | O |
| 85 | $CH_2CH_3$ | H | H | H | Cl | O |
| 86 | $CH_2Ph$ | H | H | H | H | N—OH |
| 87 | $CH_2CH_3$ | H | H | H | Cl | N—OH |
| 88 | $i-C_3H_7$ | Cl | H | H | H | N—OH |
| 89 | $i-C_3H_7$ | Cl | H | H | H | N—$OCH_3$ |
| 90 | $CH_2Ph$ | H | H | H | H | N—$OCH_3$ |

II-2-4. Preparation of the Target Compounds (II-1~3)

II-2-4-1. Syntheses of 1'-oxo-isoindigo Derivatives (Formula II-1, No. 91~No. 120)

Example 15: Synthesis of N-methyl-1'-oxo-indirubin (93)

0.24 g N-methyl-indole-2,3-dione (1.5 mmol) was dissolved in 15 ml acetic acid, added with 0.37 g anhydrous sodium acetate (4.5 mmol) solid, stirred until dissolved and then added with 0.2 g benzofuran-2-one (1.5 mmol). The reaction was maintained at 85° C. for 8 hours and then terminated. The cooled reaction mixture was poured into 200 ml ice water and thoroughly mixed. A purple solid was crystallized, filtered, desiccated and purified through column chromatography (dichloromethane: ethyl acetate=6: 1, v/v). The product was re-crystallized with dichloromethane and petroleum ether. 0.21 g of the purified dark purple solid product, N-methyl-1'-oxo-isoindigo (93), was obtained, with a yield of 62%, m.p. 232~233° C.; IR (KBr, v, cm$^{-1}$): 3442,3238, 3131, 3022, 1702, 1618, 1591, 1485, 1463, 1398, 1324, 1282, 1214, 1106, 1047, 868 594;

$^1$H-NMR(CDCl$_3$, 300 MHz) δ: 9.31 (d, J=8.00 Hz, 1H, Ar—H), 9.05 (d, J=8.00 Hz, 1H, Ar—H), 7.49-7.43 (m, 2H, Ar—H), 7.28-7.24 (m, 1H, Ar—Hs), 7.16-7.12 (m, 2H, Ar—H), 6.82 (d, J=7.50 Hz, 1H, Ar—H), 3.32 (s, 3H, N—CH$_3$);

ESI-MS m/z: 278.1 [M+H]$^+$, 300.1 [M+Na]$^+$, $C_{17}H_{11}NO_3$ (277.3)

Anal. for $C_{17}H_{11}NO_3$ Calcd (%): C, 73.64; H, 4.00; N, 5.05.

Found (%): C, 73.51; H, 4.09; N, 5.14.

Example 16: Thirty Derivatives of 1'-oxo-isoindigo (Formula II-1, No. 91~No. 120) were Synthesized by the Methods Described Above for the Syntheses of N-methyl-1'-oxo-isoindigo (93) in Example 15

Molecular structures of the compounds 91-120 are listed in Table 4. All these novel compounds were structurally characterized by IR, ESI-MS, $^1$H-NMR and elemental analysis.

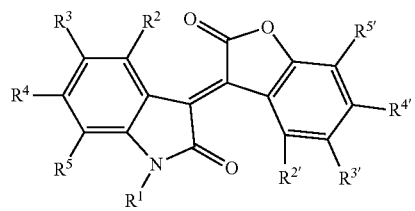

II-1

In the formula II-1, R2, $R^{2'}$, $R^{4'}$ and $R^{5'}$ represent H. Rest of the substituents are described in Table 4.

TABLE 4

Structures of 1'-oxo-7-azaindirubins (II-1: 91-120)

| ID | $R^1$ | $R^3$ | $R^4$ | $R^5$ | $R^{3'}$ |
|---|---|---|---|---|---|
| 91 | H | H | H | H | H |
| 92 | H | F | H | H | H |
| 93 | $CH_3$ | H | H | H | H |
| 94 | $CH_3$ | H | H | Cl | H |
| 95 | $CH_3$ | Cl | H | H | H |
| 96 | $CH_3$ | H | Cl | H | H |
| 97 | $CH_3$ | $CH_3$ | H | H | H |
| 98 | $CH_3$ | H | H | F | H |
| 99 | $CH_3$ | F | H | H | H |
| 100 | $CH_2CH_3$ | H | H | H | H |
| 101 | $CH_2CH_3$ | H | H | H | $OCH_3$ |
| 102 | $CH_2CH_3$ | Cl | H | H | H |
| 103 | $CH_2CH_3$ | H | Cl | H | H |
| 104 | $CH_2CH_3$ | F | H | H | H |
| 105 | $CH_2CH_3$ | H | H | F | H |
| 106 | $i-C_3H_7$ | H | H | H | H |
| 107 | $i-C_3H_7$ | Me | H | H | H |
| 108 | $i-C_3H_7$ | F | H | H | H |
| 109 | $i-C_3H_7$ | H | H | F | H |
| 110 | $i-C_3H_7$ | Cl | H | H | H |
| 111 | Triacetylribosyl | Cl | H | H | H |
| 112 | Glucosyl | H | H | H | H |
| 113 | $i-C_3H_7$ | Cl | H | H | Cl |
| 114 | $i-C_3H_7$ | H | Cl | H | Cl |
| 115 | $CH_2Ph$ | H | H | H | H |
| 116 | $CH_2Ph$ | H | H | H | $OCH_3$ |
| 117 | $CH_2Ph$ | F | H | H | H |
| 118 | $CH_2Ph$ | H | H | F | H |
| 119 | $CH_2Ph$ | Cl | H | H | H |
| 120 | $CH_2Ph$ | H | Cl | H | H |

II-2-4-2. Syntheses of 1'-oxo-5-azaisoindigo Derivatives (Formula II-2, No. 121~No. 135)

Example 17: Synthesis of N-ethyl-1'-oxo-5-azaisoindigo (127)

N-ethyl-5-azaindole-2,3-dione (0.26 g, or 1.5 mmol) was dissolved in 15 ml acetic acid, added with 0.37 g anhydrous sodium acetate (4.5 mmol) solid, stirred until dissolved and then added with 0.2 g benzofuran-2-one (1.5 mmol). The reaction was maintained at 85° C. for 8 hours and then terminated. The cooled reaction mixture was poured into 200 ml ice water and thoroughly mixed. A purple solid was crystallized, filtered, desiccated and purified through column chromatography (dichloromethane: ethyl acetate=6: 1, v/v). The product was re-crystallized with dichloromethane and petroleum ether. 0.28 g of the purified dark purple solid product, N-ethyl-1'-oxo-5-azaisoindigo (127), was obtained, with a yield of 65%, m.p. 212~214° C.; IR (KBr, v, cm$^{-1}$): 3434, 3121, 2985, 1718, 1695, 1606, 1479, 1456, 1398, 1384, 1159, 1105, 983, 762, 638;

$^1$H-NMR(CDCl$_3$, 300 MHz) δ: 9.29 (d, J=8.40 Hz, 1H, Ar—H), 9.01 (d, J=8.40 Hz, 1H, Ar—H), 7.52-7.47 (m, 2H, Ar—H), 7.23-7.20 (m, 1H, Ar—Hs), 7.05-7.02 (m, 1H, Ar—H), 6.72 (s, 1H, Ar—H), 3.86 (q, 2H, N—CH$_2$), 1.32 (t, 3H, CH$_3$);

ESI-MS m/z: 293.1 [M+H]$^+$, 315.1[M+Na]$^+$, C$_{17}$H$_{12}$N$_2$O$_3$(292.3)

Anal. for C$_{17}$H$_{12}$N$_2$O$_3$ Calcd (%): C, 69.86; H, 4.14; N, 9.58.

Found (%): C, 69.99; H, 4.05; N, 9.46.

Example 18: Fifteen Derivatives of 1'-oxo-5-azaisoindigo (Formula II-2, No. 121~No. 135) were Synthesized by the Methods Described Above for the Syntheses of N-ethyl-1'-oxo-5-azaisoindigo (127) in Example 17

Molecular structures of the compounds 121-135 are listed in Table 5. All these novel compounds were structurally characterized by IR, ESI-MS, $^1$H-NMR and elemental analysis.

II-2

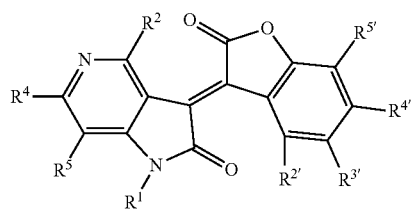

In the formula II-2, R2, R$^{2'}$ and R$^{4'}$ represent H. Rest of the substituents are described in Table 5.

TABLE 5

Structures of 1'-oxo-5-azaisoindigos (II-2: 21-135)

| ID | R$^1$ | R$^4$ | R$^5$ | R$^{3'}$ | R$^{5'}$ |
|---|---|---|---|---|---|
| 121 | H | H | H | H | H |
| 122 | H | H | F | H | H |
| 123 | CH$_3$ | H | H | H | H |
| 124 | CH$_3$ | H | Cl | H | H |
| 125 | CH$_3$ | H | F | H | H |
| 126 | CH$_3$ | H | H | CH$_3$ | H |
| 127 | CH$_2$CH$_3$ | H | H | H | H |
| 128 | CH$_2$CH$_3$ | Cl | H | H | H |
| 129 | CH$_2$CH$_3$ | H | H | H | OCH$_3$ |
| 130 | i-C$_3$H$_7$ | F | H | H | H |
| 131 | i-C$_3$H$_7$ | H | H | F | H |
| 132 | i-C$_3$H$_7$ | H | Cl | H | H |
| 133 | i-C$_3$H$_7$ | F | H | H | H |
| 134 | CH$_2$Ph | H | H | H | H |
| 135 | CH$_2$Ph | H | H | H | OCH$_3$ |

II-2-4-3. Syntheses of 1'-oxo-5-azaisoindigo Derivatives (Formula II-3, No. 136~No. 153)

Example 17: Synthesis of N-methyl-1'-oxo-7-azaisoindigo (139)

N-methyl-7-azaindole-2,3-dione (0.24 g, or 1.5 mmol) was Dissolved in 15 ml acetic Acid, added with 0.37 g anhydrous sodium acetate (4.5 mmol) solid, stirred until dissolved and then added with 0.2 g benzofuran-2-one (1.5 mmol). The reaction was maintained at 85° C. for 8 hours and then terminated. The cooled reaction mixture was poured into 200 ml ice water and thoroughly mixed. A purple solid was crystallized, filtered, desiccated and purified through column chromatography (dichloromethane: ethyl acetate=6: 1, v/v). The product was re-crystallized with dichloromethane and petroleum ether. 0.25 g of the purified dark purple solid product, N-methyl-1'-oxo-7-azaisoindigo (139), was obtained, with a yield of 61%, m.p. 261~263° C.; IR (KBr, v, cm$^{-1}$): 3438, 3175, 3126, 1697, 1618, 1598, 1457, 1403, 1384, 1347, 1101, 984;

$^1$H-NMR (DMSO-d6, 300 MHz) δ: 9.32 (d, J=8.20 Hz, 1H, Ar—H), 9.04 (d, J=8.20 Hz, 1H, Ar—H), 7.50-7.44 (m, 2H, Ar—H), 7.29-7.25 (m, 1H, Ar—Hs), 7.17-7.14 (m, 1H, Ar—H), 6.83 (d, J=7.80 Hz, 1H, Ar—H), 3.35 (s, 3H, N—CH$_3$);

ESI-MS m/z: 279.1 [M+H]$^+$, 301.1 [M+Na]$^+$, C$_{16}$H$_{10}$N$_2$O$_3$(278.3)

Anal. for C$_{16}$H$_{10}$N$_2$O$_3$ Calcd (%): C, 69.06; H, 3.62; N, 10.07.

Found (%): C, 69.11; H, 3.51; N, 10.16.

Example 20: Eighteen Derivatives of 1'-oxo-7-azaisoindigo (Formula II-3, No. 136~No. 153) were Synthesized by the Methods Described Above for the Syntheses of N-methyl-1'-oxo-7-azaisoindigo (139) in Example 19

Molecular structures of the compounds 136-153 are listed in Table 6. All these novel compounds were structurally characterized by IR, ESI-MS, $^1$H-NMR and elemental analysis.

II-3

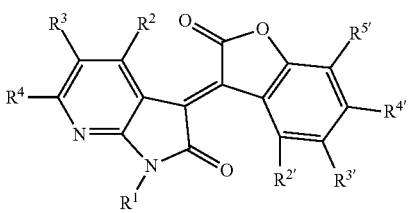

In the formula II-3, R$^2$, R$^{2'}$ and R$^{4'}$ represent H. Rest of the substituents are described in Table 6

TABLE 6

Structures of 1'-oxo-7-azaisoindigos (II-3: 136-153)

| ID | R$^1$ | R$^3$ | R$^4$ | R$^{3'}$ | R$^{5'}$ |
|---|---|---|---|---|---|
| 136 | H | H | H | H | H |
| 137 | H | F | H | H | H |
| 138 | H | H | Cl | H | H |
| 139 | CH$_3$ | H | H | H | H |
| 140 | CH$_3$ | H | H | H | CH$_3$ |
| 141 | CH$_3$ | H | H | CH$_3$ | H |
| 142 | CH$_3$ | CH$_3$ | H | H | H |
| 143 | CH$_3$ | Cl | H | H | H |
| 144 | CH$_3$ | F | H | H | H |
| 145 | CH$_2$CH$_3$ | H | H | H | H |

TABLE 6-continued

Structures of 1'-oxo-7-azaisoindigos (II-3: 136-153)

| ID | R$^1$ | R$^3$ | R$^4$ | R$^{3'}$ | R$^{5'}$ |
|---|---|---|---|---|---|
| 146 | CH$_2$CH$_3$ | F | H | H | H |
| 147 | CH$_2$CH$_3$ | Cl | H | H | H |
| 148 | CH$_2$CH$_3$ | H | H | H | OCH$_3$ |
| 149 | i-C$_3$H$_7$ | F | H | H | H |
| 150 | i-C$_3$H$_7$ | H | H | F | H |
| 151 | i-C$_3$H$_7$ | Cl | H | H | H |
| 152 | CH$_2$Ph | H | H | H | H |
| 153 | CH$_2$Ph | F | H | H | H |

III. Exemplification of Antitumor Activities in Cell-Based Assays

Example 21: Inhibitory Effects of the Compounds (I-1~3 and II-1~3) on Tumor Cell Growth III-1. Materials and Instruments III-1-1. Tumor Cell Lines human hepatocellular carcinoma cell line HepG-2, human lung adenocarcinoma epithelial cell line A549

III-1-2. Reagents

RPMI Medium 1640 (GIBCOBRL, Inc. U.S.A.), calf serum (Hangzhou Sijiqing Biological Engineering Materials Co., Ltd.), MTT (Sigma), HEPES (Shanghai Livzon Pharmaceutical Co., Ltd.), L-glutamine (imported from Japan), dimethyl sulfoxide (DMSO, analytical reagent);

Measured samples: 90 compounds from 1'-oxo-indirubins (I) and 1'-oxo-isoindigos (II) (prepared in-house, listed in Table 7);

Reference substances: 1-ethyl-indirubin (154) and 1-ethyl-indirubin-3'-oxime (155) (prepared in-house, structures characterized);

III-1-3. Preparation of Reagents

III-1-3-1. Cell Culture Medium 10.4 g of 1640 medium powder, 2.1 g of sodium bicarbonate, 0.3 g of glutamine, 5.95 g of HEPES, 100,000 units of penicillin and 100,000 units of streptomycin were added to 1000 ml double distilled water. The mixture was sterilized by filtration using Millipore filter, and aliquots were stored at −20° C. The inactivated calf serum was added to the medium prior to use;

III-1-3-2. Calf Serum

It was inactivated for 30 minutes in 56° C. water bath, and the aliquots were stored at −20° C.;

III-1-3-3. MTT

It was diluted to 5 mg/ml with PBS, stored at 4° C. and kept away from light. It was used within two weeks;

III-1-3-4. PBS 8.00 g of sodium chloride, 0.20 g of potassium chloride, 3.4 g disodium phosphate dodecahydrate and 0.20 g of potassium phosphate dibasic were fully dissolved in double distilled water at 37° C., diluted to 1000 ml, and aliquots were stored at 4° C.;

III-1-3-5

90 measured samples, the reference substances (154 and 155) were dissolved in DMSO, and stored at −20° C.

III-1-4. Main Equipment

CO$_2$ incubator (GB16, Heraeus company, German); clean bench (SW-CJ-1F, Suzhou Antai Air Tech Co., Ltd.); horizontal centrifuge (LXJ-II, Shanghai Third Medical Instruments Factory); enzyme-linked immune detector (BIO RAD Model 550, USA); inverted biological microscope (XSZ-D2, Chongqing Optical Instrument Factory); rapid mixer (SK-1 type, Changzhou Guohua Electric Appliance Co., Ltd.); electrical heating water thermostat system (DK-8D, Shanghai Medical Constant Temperature Equipment Factory): flow cytometry (FACSCalibur, American BD Company); plate oscillator (752-A, Shanghai Medical Analysis Instrument Factory); electronic balance (BS110S, Sartorius Company, German).

III-2. Methods

III-2-1. Cell Culture

Tumor cells were seeded in RPM11640 medium containing 10% calf serum, incubated at 37° C., 5% CO$_2$ in CO$_2$ incubator, and passaged every 2-3 days. Cells at logarithmic growth phase were used for this experiment.

III-2-2. Grouping

The cells at logarithmic growth phase were formulated into suspension. The cell viability by trypan blue staining was more than 98%. The cell suspension was divided into several groups: 1 as blank control group (cell suspension plus solvent DMSO); and 2 as experimental groups (cell suspension plus compounds to be tested).

III-2-3. Determination of IC50 Values by MTT (the 50% Inhibitory Concentration)

The drugs were formulated into a stock solution in DMSO, and the concentration of the stock solution was 20 mmol (used within 4 hours). In the experiment, the work solution of the drugs was diluted with RPMI1640 medium containing 10% calf serum under aseptic condition, to a final concentration of 80 µM. The drug concentrations were increased by 2 times (1.25-20 µM).

The cells in logarithmic growth phase were selected, centrifuged, counted, and formulated into a cell suspension (2.5×10$^4$/ml) with RPMI1640 medium containing 10% calf serum. The cell suspension were inoculated into 96-well plates at a density of 5000 cells/200 µl per well, incubated for 24 hours at 37° C., 5% CO$_2$. According to the above concentration of the drug, the cells were inoculated to 6 groups (including one control group), with 8 wells per group. After incubating for 72 hours, the viability of cells was measured by MTT assay. The absorbance value (A) was measured with detection wavelength at 540 nm, reference wavelength at 630 nm. The inhibitory rate (I) was calculated by the following equation, where T was the absorbance value of the experimental groups, and C was the absorbance value of the blank control group:

$I=(1-T/C)\times 100\%$

Equation of regression line was drawn from concentration-inhibitory rate curve, from which the $IC_{50}$ of tested sample was calculated.

III-3. Results

Inhibitory potencies ($IC_{50}$, μM) of the 90 compounds described above on the proliferation of the tumor cell lines A549 and HepG2 are listed in Table 7.

TABLE 7

$IC_{50}$ (μM) of 1'-oxo-indirubins (I) and 1'-oxo-isoindigos (II) on the tumor cells A549 and HepG2

| ID | A549 | HepG2 |
|---|---|---|
| 1 | 40.0 ± 1.4 | >100 |
| 2 | >100 | ND |
| 3 | 21.9 ± 0.9 | 26.4 ± 1.1 |
| 4 | 9.5 ± 2.1 | 31.5 ± 2.9 |
| 5 | 11.5 ± 1.0 | 87.0 ± 2.1 |
| 6 | 11.9 ± 1.4 | 60.0 ± 1.7 |
| 7 | 8.0 ± 1.2 | 19.0 ± 1.6 |
| 8 | 10.0 ± 1.4 | 32.2 ± 2.4 |
| 9 | 18.5 ± 1.8 | 25.0 ± 1.0 |
| 10 | 8.1 ± 0.6 | 28.5 ± 1.3 |
| 11 | 8.5 ± 1.6 | 45.0 ± 1.9 |
| 12 | 14.0 ± 1.7 | 26.0 ± 2.7 |
| 13 | 11.0 ± 1.2 | 42.0 ± 1.8 |
| 14 | 7.0 ± 1.6 | 24.0 ± 1.5 |
| 15 | 7.4 ± 1.7 | 34.0 ± 0.9 |
| 16 | 16.0 ± 2.0 | 61.0 ± 2.9 |
| 17 | 8.0 ± 2.3 | 25.0 ± 2.7 |
| 18 | 7.05 ± 1.1 | 17.0 ± 1.9 |
| 19 | 16.0 ± 1.5 | 8.0 ± 1.5 |
| 20 | 1.8 ± 1.0 | 12.0 ± 1.4 |
| 21 | 4.0 ± 2.4 | 12.0 ± 1.9 |
| 22 | 2.7 ± 1.2 | 7.1 ± 1.1 |
| 23 | 3.1 ± 0.8 | 6.9 ± 0.8 |
| 24 | 3.8 ± 1.5 | 12.1 ± 0.9 |
| 25 | 3.7 ± 0.9 | 5.0 ± 0.9 |
| 26 | 5.4 ± 0.6 | 29.0 ± 1.8 |
| 27 | 7.1 ± 0.7 | 19.0 ± 1.1 |
| 28 | 7.0 ± 1.3 | 30.0 ± 1.5 |
| 29 | 3.6 ± 0.2 | 7.7 ± 1.2 |
| 30 | 3.8 ± 0.5 | 3.0 ± 0.5 |
| 31 | 1.2 ± 0.8 | 2.8 ± 0.4 |
| 32 | 10.5 ± 1.3 | 12.8 ± 1.6 |
| 33 | 14.8 ± 1.2 | 21.0 ± 0.9 |
| 34 | 14.1 ± 1.5 | 51.1 ± 2.6 |
| 35 | 17.5 ± 1.8 | 29.2 ± 1.4 |
| 36 | 10.0 ± 0.6 | 31.5 ± 1.8 |
| 37 | 9.0 ± 2.1 | 41.0 ± 1.7 |
| 38 | 9.05 ± 1.4 | 32.2 ± 1.5 |
| 39 | 33.0 ± 2.9 | 19.0 ± 2.1 |
| 40 | 14.0 ± 1.2 | >100 |
| 41 | 8.3 ± 1.7 | 45.0 ± 3.0 |
| 42 | 15.0 ± 1.2 | 28.0 ± 2.5 |
| 43 | 14.0 ± 1.7 | 42.0 ± 4.2 |
| 44 | >100 | >100 |
| 45 | 4.8 ± 0.6 | 3.6 ± 0.2 |
| 46 | 3.4 ± 0.7 | 3.8 ± 0.5 |
| 47 | 1.7 ± 0.8 | 1.6 ± 0.8 |
| 48 | 1.9 ± 0.4 | 2.6 ± 0.4 |
| 49 | 9.5 ± 0.6 | 4.8 ± 0.7 |
| 50 | 7.7 ± 1.2 | 2.9 ± 0.5 |
| 51 | 3.9 ± 0.5 | 1.7 ± 0.6 |
| 52 | 2.8 ± 0.4 | 2.1 ± 0.2 |
| 53 | 2.1 ± 0.5 | 16.0 ± 1.5 |
| 54 | 12.0 ± 1.4 | 1.8 ± 1.9 |
| 55 | 12.0 ± 1.9 | 4.0 ± 2.4 |
| 56 | 7.1 ± 1.1 | 2.7 ± 1.2 |
| 57 | 6.9 ± 0.8 | 3.1 ± 0.8 |
| 58 | 12.1 ± 0.9 | 3.8 ± 1.5 |

TABLE 7-continued $IC_{50}$ (μM) of 1'-oxo-indirubins (I) and 1'-oxo-isoindigos (II) on the tumor cells A549 and HepG2

| ID | A549 | HepG2 |
|---|---|---|
| 59 | 5.0 ± 0.9 | 3.7 ± 0.9 |
| 60 | 29.0 ± 1.8 | 5.4 ± 0.6 |
| 62 | 9.5 ± 2.1 | 11.5 ± 1.0 |
| 65 | 18.5 ± 1.8 | 40.0 ± 3.1 |
| 66 | 7.4 ± 1.7 | 1.8 ± 0.6 |
| 68 | 14.0 ± 1.7 | 18.5 ± 1.8 |
| 70 | 4.5 ± 0.6 | 3.6 ± 0.4 |
| 74 | 9.4 ± 0.6 | 19.0 ± 1.1 |
| 75 | 8.0 ± 1.2 | 10 ± 1.4 |
| 79 | 17.4 ± 1.7 | 31.5 ± 2.5 |
| 82 | 16 ± 2.0 | 18.0 ± 2.3 |
| 85 | 25.0 ± 2.7 | 18.5 ± 1.5 |
| 88 | 87.0 ± 2.1 | 80.1 ± 1.5 |
| 90 | 29.0 ± 1.8 | 30.2 ± 1.5 |
| 92 | 31.7 ± 1.5 | 15.2 ± 1.2 |
| 96 | 17.2 ± 1.6 | 14.2 ± 1.3 |
| 100 | 7.0 ± 1.4 | 9.2 ± 2.0 |
| 106 | 35.5 ± 2.9 | 3.8 ± 1.5 |
| 112 | 90.1 ± 4.5 | >100 |
| 116 | 3.7 ± 0.6 | 7.4 ± 1.7 |
| 119 | 39.6 ± 1.7 | 27.5 ± 1.3 |
| 120 | 49.1 ± 2.6 | 43 ± 2.2 |
| 121 | 11.6 ± 1.1 | 15.6 ± 1.2 |
| 123 | 5.8 ± 0.8 | 9.1 ± 1.0 |
| 127 | 4.7 ± 0.9 | 8.4 ± 1.3 |
| 130 | 28.5 ± 1.6 | 19.6 ± 1.3 |
| 134 | 11.5 ± 1.2 | 26.0 ± 2.1 |
| 138 | 12.1 ± 1.4 | 25.8 ± 1.7 |
| 140 | 1.9 ± 0.8 | 7.3 ± 0.8 |
| 146 | 26.3 ± 2.1 | 35.2 ± 2.3 |
| 150 | 7.9 ± 1.3 | 5.6 ± 0.6 |
| 152 | 18.2 ± 1.2 | 42.3 ± 1.8 |
| — | | |
| 154 | 19.0 ± 1.1 | 7.1 ± 0.7 |
| 155 | 30.3 ± 1.5 | 7.0 ± 1.3 |

Note: Molecular structures of the reference samples, 154 and 155, are described below: 1-ethyl-indirubin (154), 1-ethyl-indirubin-3'-oxime (155)

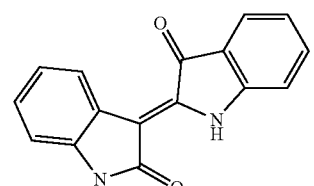

154

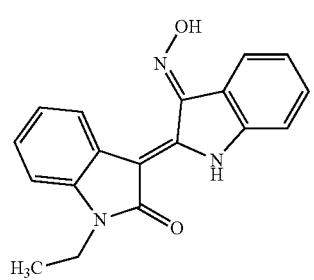

155

IV. Exemplification of Computational Modeling

Example 22: Computer-Aided Drug Design (CADD) Indicates that 1'-oxo-7-azaindirubin can Bind CDK2 at the Same Domain as 7-azaindirubin Binds, the Binding Affinities are Similar for 1'-oxo-7-azaindirubin and 7-azaindirubin (FIG. 1)

Although 1'-oxo-7-azaindirubin and 7-azaindirubin are chemically distinct, their three dimensional structures are similar. This similarity may confer them with similar abilities to interact with molecular targets and to therefore have similar biological activity. Based on this hypothesis, we have performed a docking study to demonstrate the interaction between CDK2 and 1'-oxo-7-azaindirubin (75), or 7-azaindirubin (molecular structure as below). FIG. 1 shows that the two compounds bind to the same ATP-binding domain of CDK2 with similar affinities. This result suggests that the replacement of the NH in the scaffold of 7-azaindirubin with an oxygen atom will not result in significant changes to the molecular mechanism of action of this type of chemical compound. It also suggests that computational modeling, through, for example, docking studies, may be a useful means for further structural modification of 1'-oxo-(aza)indirubins (I) and 1'-oxo-(aza)isoindigos (II).

1'-oxo-7-azaindirubin (75) and 7-azaindirubin

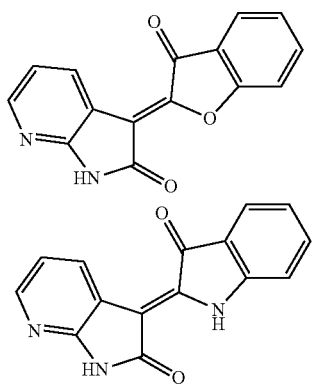

7-Azaindirubin

Example 23: Computer-Aided Drug Design (CADD) Indicates that N-methyl-1'-oxo-isoindigo can Bind STAT3-SH2 Domain in the Same Way as N-methylisoindigo, with Similar Binding Affinities (FIG. 2).

N-methyl-isoindigo (molecular structure as below) is a known STAT3 allosteric inhibitor. It can fit in the binding pocket of human STAT3 SH2 domain and form hydrogen bonds with specific amino acid residues of the protein. The docking score is 93.9797. N-methyl-1'-oxoisoindigo shares a similar three dimensional structure with N-methyl-isoindigo, and therefore potentially has functions similar to N-methyl-isoindigo, i.e., inhibiting STAT3 function through SH2 domain binding. Based on this hypothesis, we performed a docking study of N-methyl-1'-oxoisoindigo with human STAT3-SH2. The results indicate that the bindings of N-methyl-1'-oxoisoindigo and N-methyl-isoindigo with human STAT3-SH2 are indeed similar, suggesting that the replacement of the nitrogen atom at position 1' of N-methyl-isoindigo with an oxygen atom does not significantly change the mode-of-action for these types of molecules.

N-methylisoindigo and N-methyl-1'-oxoisoindigo (93)

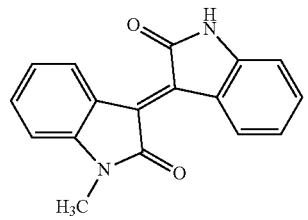

N-methylisoindigo

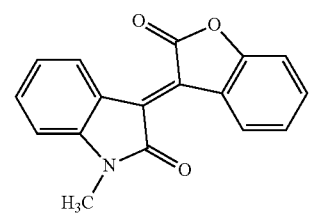

93

What has been described above illustrates and demonstrates the basic principles, the main features and the potential advantages of the present invention. Technical professionals in this field should understand that the present invention is not limited to the examples listed in the text. These examples as well as other descriptions in the present invention serve to illustrate the scientific fundamentals of the present invention; various changes and improvements can also be made within the scope and the spirit of the present invention, and all these changes and improvements fall into the category of the claims of the present invention. The protection category of the present invention is defined by the attached Claims and their equivalents.

The invention claimed is:

1. A compound of formula I-1 or formula II-1, or an enantiomer, a racemate, a cis-trans isomer or any combination thereof, or a pharmaceutically acceptable salt thereof:

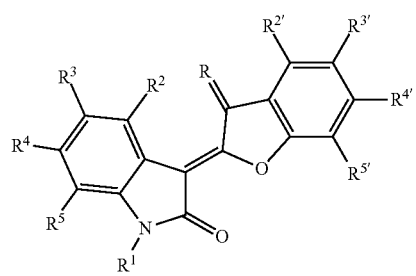

I-1

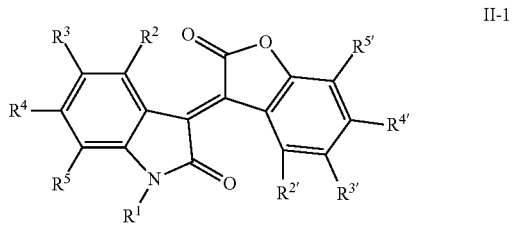

II-1 wherein, $R^1$ is selected from the group consisting of H, D, or the following groups that may be unsubstituted or substituted by 1 to 3 substituents: $C_1$~$C_6$ alkyl, aryl, aralkyl, acyl, glycosyl protected by acyl, or glycosyl; wherein said substituents are selected from the group consisting of halogen, hydroxyl, $C_1$~$C_3$ alkyl, nitro or amino;

$R^2$, $R^{2'}$, $R^{4'}$ and $R^{5'}$ are H;

$R^3$ is selected from the group consisting of H, halo, and $C_1$~$C_4$ alkyl;

$R^4$ is selected from the group consisting of H, halo, and $C_1$~$C_4$ alkyl;

$R^5$ is selected from the group consisting of H, halo, and $C_1$~$C_4$ alkyl;

$R^{3'}$ is selected from the group consisting of H, halo, $C_1$~$C_4$ alkoxyl and $C_1$~$C_4$ alkyl; and R is selected from the group consisting of oxygen, sulfur, selenium, or $NOR^6$ group, wherein $R^6$ is H or $C_1$~$C_6$ straight-chain or branched-chain alkyl.

2. The compound of claim 1, wherein in formula I-1, $R^1$ is selected from the group consisting of H, D, $C_1$~$C_6$ alkyl, phenyl, phenyl-$CH_2$—, arabinosyl, xylosyl, ribosyl, mannosyl, and glucosyl;

$R^3$ is selected from the group consisting of H, halo, and $C_1$~$C_4$ alkyl;

$R^4$ is selected from the group consisting of H and halo;

$R^5$ is selected from the group consisting of H and halo;

$R^{3'}$ is selected from the group consisting of H and halo; and

R is selected from the group consisting of oxygen and $NOR^6$ group, wherein $R^6$ is H or $C_1$~$C_6$ straight-chain or branched-chain.

3. The compound of claim 1, wherein the compound is selected from the group consisting of the following Compound ID Nos. 1-60:

| Compound ID No. | $R^1$ | $R^3$ | $R^4$ | $R^5$ | $R^{3'}$ | R |
|---|---|---|---|---|---|---|
| 1 | H | H | H | H | H | O |
| 2 | H | H | H | F | H | O |
| 3 | $CH_2CH_3$ | H | H | H | H | O |
| 4 | $CH_2CH_3$ | H | H | F | H | O |
| 5 | $CH_2CH_3$ | Cl | H | H | H | O |
| 6 | $CH_2CH_3$ | H | Cl | H | H | O |
| 7 | $CH_2CH_3$ | $CH_3$ | H | H | H | O |
| 8 | i-$C_3H_7$ | H | H | H | H | O |
| 9 | i-$C_3H_7$ | F | H | H | H | O |
| 10 | i-$C_3H_7$ | H | H | F | H | O |
| 11 | i-$C_3H_7$ | Cl | H | H | H | O |
| 12 | i-$C_3H_7$ | H | Cl | H | H | O |
| 13 | i-$C_3H_7$ | Me | H | H | H | O |
| 14 | $CH_2Ph$ | H | H | H | H | O |
| 15 | $CH_2Ph$ | F | H | H | H | O |
| 16 | $CH_2Ph$ | Cl | H | H | H | O |
| 17 | $CH_2Ph$ | Me | H | H | H | O |
| 18 | $CH_2CH_3$ | F | H | H | H | O |
| 19 | $CH_2CH_3$ | H | H | H | Cl | O |
| 20 | $CH_2CH_3$ | H | F | Cl | H | O |
| 21 | $CH_2CH_3$ | Cl | H | H | Cl | O |
| 22 | $CH_2CH_3$ | H | Cl | H | Cl | O |
| 23 | i-$C_3H_7$ | Cl | H | H | Cl | O |
| 24 | i-$C_3H_7$ | H | Cl | H | Cl | O |
| 25 | H | H | H | H | H | N—OH |
| 26 | H | H | H | F | H | N—OH |
| 27 | $CH_2CH_3$ | H | H | H | H | N—OH |
| 28 | $CH_2CH_3$ | H | H | F | H | N—OH |
| 29 | $CH_2CH_3$ | Cl | H | H | H | N—OH |
| 30 | $CH_2CH_3$ | H | Cl | H | H | N—OH |
| 31 | $CH_2CH_3$ | $CH_3$ | H | H | H | N—OH |
| 32 | i-$C_3H_7$ | H | H | H | H | N—OH |
| 33 | Ribosyl | H | H | H | H | N—OH |
| 34 | i-$C_3H_7$ | H | H | F | H | N—OH |
| 35 | i-$C_3H_7$ | Cl | H | H | H | N—OH |
| 36 | i-$C_3H_7$ | H | Cl | H | H | N—OH |
| 37 | i-$C_3H_7$ | Me | H | H | H | N—OH |
| 38 | $CH_2Ph$ | H | H | H | H | N—OH |
| 39 | $CH_2Ph$ | F | H | H | H | N—OH |
| 40 | $CH_2Ph$ | Cl | H | H | H | N—OH |
| 41 | $CH_2Ph$ | Me | H | H | H | N—OH |
| 42 | $CH_2CH_3$ | F | H | H | H | N—OH |
| 43 | $CH_2CH_3$ | H | H | H | Cl | N—OH |
| 44 | $CH_2CH_3$ | H | H | F | Cl | N—OH |
| 45 | $CH_2CH_3$ | Cl | H | H | Cl | N—OH |
| 46 | $CH_2CH_3$ | H | Cl | H | Cl | N—OH |
| 47 | i-$C_3H_7$ | Cl | H | H | H | N—OH |
| 48 | i-$C_3H_7$ | H | Cl | H | Cl | N—OH |
| 49 | H | H | H | H | H | N—$OCH_3$ |
| 50 | H | H | H | F | H | N—$OCH_3$ |
| 51 | $CH_2CH_3$ | H | H | H | H | N—$OCH_3$ |
| 52 | $CH_2CH_3$ | H | H | F | H | N—$OCH_3$ |
| 53 | Glucosyl | Cl | H | H | H | N—$OCH_3$ |
| 54 | i-$C_3H_7$ | H | Cl | H | H | N—$OCH_3$ |
| 55 | i-$C_3H_7$ | Me | H | H | H | N—$OCH_3$ |
| 56 | $CH_2Ph$ | H | H | H | H | N—$OCH_3$ |
| 57 | $CH_2Ph$ | F | H | H | H | N—$OCH_3$ |
| 58 | $CH_2Ph$ | Cl | H | H | H | N—$OCH_3$ |
| 59 | $CH_2CH_3$ | F | H | H | H | N—$OCH_3$ |
| 60 | i-$C_3H_7$ | H | Cl | H | Cl | N—$OCH_3$. |

4. The compound of claim 1, wherein the compound is selected from the group consisting of the following Compound ID Nos. 91-120:

| Compound ID No. | $R^1$ | $R^3$ | $R^4$ | $R^5$ | $R^{3'}$ |
|---|---|---|---|---|---|
| 91 | H | H | H | H | H |
| 92 | H | F | H | H | H |
| 93 | $CH_3$ | H | H | H | H |
| 94 | $CH_3$ | H | H | Cl | H |
| 95 | $CH_3$ | Cl | H | H | H |
| 96 | $CH_3$ | H | Cl | H | H |
| 97 | $CH_3$ | $CH_3$ | H | H | H |
| 98 | $CH_3$ | H | H | F | H |
| 99 | $CH_3$ | F | H | H | H |
| 100 | $CH_2CH_3$ | H | H | H | H |
| 101 | $CH_2CH_3$ | H | H | H | $OCH_3$ |
| 102 | $CH_2CH_3$ | Cl | H | H | H |
| 103 | $CH_2CH_3$ | H | Cl | H | H |
| 104 | $CH_2CH_3$ | F | H | H | H |
| 105 | $CH_2CH_3$ | H | H | F | H |
| 106 | i-$C_3H_7$ | H | H | H | H |
| 107 | i-$C_3H_7$ | Me | H | H | H |
| 108 | i-$C_3H_7$ | F | H | H | H |
| 109 | i-$C_3H_7$ | H | H | F | H |
| 110 | i-$C_3H_7$ | Cl | H | H | H |
| 111 | Triacetylribosyl | Cl | H | H | H |
| 112 | Glucosyl | H | H | H | H |
| 113 | i-$C_3H_7$ | Cl | H | H | Cl |
| 114 | i-$C_3H_7$ | H | Cl | H | Cl |
| 115 | $CH_2Ph$ | H | H | H | H |
| 116 | $CH_2Ph$ | H | H | H | $OCH_3$ |
| 117 | $CH_2Ph$ | F | H | H | H |
| 118 | $CH_2Ph$ | H | H | F | H |
| 119 | $CH_2Ph$ | Cl | H | H | H |
| 120 | $CH_2Ph$ | H | Cl | H | H. |

5. The compound of claim 1, wherein the pharmaceutically acceptable salt is a salt formed with an inorganic acid or an organic acid; the inorganic acid includes hydrochloric acid, hydrobromic acid, phosphoric acid, nitric acid, and sulfuric acid; the organic acid includes methanoic acid, acetic acid, propionic acid, succinic acid, naphthalene disulfonic acid (1, 5), asiatic acid, carbenoxolone, glycyrrhetinic acid, tartaric acid, oleanolic acid, crataegolic acid, ursolic acid, corosolic acid, betulinic acid, boswellic acid, oxalic acid, lactic acid, salicylic acid, benzoic acid, butylcarboxylic acid, diethylacetic acid, malonic acid, amber acid, fumaric acid, pimelic acid, hexanedioic acid, maleic acid, malic acid, aminosulfonic acid, phenylpropionic acid, gluconic acid, ascorbic acid, nicotinic acid, isonicotinic acid, methanesulfonic acid, ethanesulfonic acid, para-toluenesulfonic acid, citric acid and amino acid.

6. A pharmaceutical composition comprising (a) the compound of claim 1, or enantiomer, racemate, cis-trans isomer or any combination thereof, or pharmaceutically acceptable salt thereof; and (b) pharmaceutically acceptable carriers.

7. The pharmaceutical composition of claim 6, wherein dosage form of said composition is low capacity injection, medium capacity injection, high capacity injection, dried powder injection, emulsion for injection, tablet, pill, capsule, paste, cream, patch, liniment, powder, spray, implant, drop, suppository, ointment, various nano preparations, or liposomes.

8. The compound of claim 1, wherein in formula II-1,
$R^1$ is selected from the group consisting of H, D, $C_1\sim C_6$ alkyl, phenyl, phenyl-$CH_2$—, arabinosyl, xylosyl, ribosyl, mannosyl, and glucosyl;
$R^3$ is selected from the group consisting of H, halo, and $C_1\sim C_4$ alkyl;
$R^4$ is selected from the group consisting of H and halo;
$R^5$ is selected from the group consisting of H and halo; and
$R^{3'}$ is selected from the group consisting of H, halo and $C_1\sim C_4$ alkoxyl.

9. The pharmaceutical composition of claim 6 comprising (a) the compound of claim 2, or enantiomer, racemate, cis-trans isomer or any combination thereof, or pharmaceutically acceptable salt thereof; and (b) pharmaceutically acceptable carriers.

10. The pharmaceutical composition of claim 6 comprising (a) the compound of claim 3, or enantiomer, racemate, cis-trans isomer or any combination thereof, or pharmaceutically acceptable salt thereof; and (b) pharmaceutically acceptable carriers.

11. The pharmaceutical composition of claim 6 comprising (a) the compound of claim 4, or enantiomer, racemate, cis-trans isomer or any combination thereof, or pharmaceutically acceptable salt thereof; and (b) pharmaceutically acceptable carriers.

12. The pharmaceutical composition of claim 6 comprising (a) the compound of claim 5, or enantiomer, racemate, cis-trans isomer or any combination thereof, or pharmaceutically acceptable salt thereof; and (b) pharmaceutically acceptable carriers.

13. The pharmaceutical composition of claim 6 comprising (a) the compound of claim 8, or enantiomer, racemate, cis-trans isomer or any combination thereof, or pharmaceutically acceptable salt thereof; and (b) pharmaceutically acceptable carriers.

* * * * *